(12) United States Patent
Blomquist

(10) Patent No.: US 11,986,292 B2
(45) Date of Patent: *May 21, 2024

(54) INSULIN PUMP BASED EXPERT SYSTEM

(71) Applicant: Tandem Diabetes Care, Inc., San Diego, CA (US)

(72) Inventor: Michael Blomquist, Blaine, MN (US)

(73) Assignee: Tandem Diabetes Care, Inc., San Diego, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/715,735

(22) Filed: Apr. 7, 2022

(65) Prior Publication Data
US 2022/0225906 A1 Jul. 21, 2022

Related U.S. Application Data

(60) Continuation of application No. 16/560,555, filed on Sep. 4, 2019, now Pat. No. 11,576,594, which is a
(Continued)

(51) Int. Cl.
*A61B 5/145* (2006.01)
*A61B 5/00* (2006.01)
(Continued)

(52) U.S. Cl.
CPC ........ *A61B 5/14532* (2013.01); *A61B 5/4839* (2013.01); *A61B 5/7475* (2013.01);
(Continued)

(58) Field of Classification Search
CPC .............. A61M 5/1723; A61M 5/7275; A61M 5/4839; A61M 5/14532; A61M 2230/201;
(Continued)

(56) References Cited

U.S. PATENT DOCUMENTS 2,462,596 A 2/1949 Bent
2,629,376 A 2/1953 Pierre et al.
(Continued)

FOREIGN PATENT DOCUMENTS

DE 399065 A1 7/1924
DE 4407005 C1 3/1995
(Continued)

OTHER PUBLICATIONS

Application and File history for U.S. Appl. No. 11/755,480, filed May 30, 2007.
(Continued)

*Primary Examiner* — Nathan R Price
*Assistant Examiner* — Anh Bui
(74) *Attorney, Agent, or Firm* — MERCHANT & GOULD P.C.

(57) ABSTRACT

An apparatus comprising a pump configured to deliver insulin, an input configured to receive blood glucose data, a user interface, and a controller communicatively coupled to the pump, the input, and the user interface. The controller includes a blood glucose data module to compare the blood glucose data to a target blood glucose level for an insulin pump user. The controller is configured to present a question related to the blood glucose level via the user interface when the blood glucose level is different than the target blood glucose level, receive a response to the question via the user interface, and present a recommended user action based at least in part on the response. Other devices, systems, and methods are disclosed.

16 Claims, 4 Drawing Sheets

Related U.S. Application Data continuation of application No. 15/830,415, filed on Dec. 4, 2017, now Pat. No. 11,298,053, which is a continuation-in-part of application No. 14/187,414, filed on Feb. 24, 2014, now Pat. No. 9,833,177, which is a continuation of application No. 13/465,570, filed on May 7, 2012, now Pat. No. 8,657,779, which is a division of application No. 11/755,480, filed on May 30, 2007, now Pat. No. 8,221,345.

(51) Int. Cl.
| | |
|---|---|
| *A61M 5/172* | (2006.01) |
| *G16H 10/20* | (2018.01) |
| *G16H 20/17* | (2018.01) |
| *G16H 40/63* | (2018.01) |
| *G16H 40/67* | (2018.01) |
| *G16H 50/20* | (2018.01) |
| *A61M 5/142* | (2006.01) |

(52) U.S. Cl.
CPC .......... *A61M 5/1723* (2013.01); *G16H 10/20* (2018.01); *G16H 20/17* (2018.01); *G16H 40/63* (2018.01); *G16H 40/67* (2018.01); *G16H 50/20* (2018.01); *A61B 5/7275* (2013.01); *A61B 2560/045* (2013.01); *A61M 2005/14208* (2013.01); *A61M 2205/3561* (2013.01); *A61M 2205/52* (2013.01); *A61M 2230/201* (2013.01)

(58) Field of Classification Search
CPC ............ A61M 2205/18; G06F 19/3468; G06F 19/3456
See application file for complete search history.

(56) References Cited

U.S. PATENT DOCUMENTS

| | | |
|---|---|---|
| 2,691,542 A | 10/1954 | Chenoweth |
| 3,059,639 A | 10/1962 | Blackman et al. |
| 4,392,849 A | 7/1983 | Petre et al. |
| 4,393,365 A | 7/1983 | Kondo et al. |
| 4,403,984 A | 9/1983 | Ash et al. |
| 4,475,901 A | 10/1984 | Kraegen et al. |
| 4,538,616 A | 9/1985 | Rogoff |
| 5,000,664 A | 3/1991 | Lawless et al. |
| 5,050,612 A | 9/1991 | Matsumura |
| 5,122,362 A | 6/1992 | Phillips et al. |
| 5,153,827 A | 10/1992 | Coutre et al. |
| 5,181,910 A | 1/1993 | Scanlon |
| 5,207,666 A | 5/1993 | Idriss et al. |
| 5,219,330 A | 6/1993 | Bollish et al. |
| 5,311,175 A | 5/1994 | Waldman |
| 5,338,157 A | 8/1994 | Blomquist |
| 5,362,562 A | 11/1994 | Evans et al. |
| 5,364,346 A | 11/1994 | Schrezenmeir |
| 53,685,562 | 11/1994 | Blomquist et al. |
| 5,376,070 A | 12/1994 | Purvis et al. |
| 5,389,078 A | 2/1995 | Zalesky et al. |
| 5,395,326 A | 3/1995 | Haber et al. |
| 5,482,446 A | 1/1996 | Williamson et al. |
| 5,485,408 A | 1/1996 | Blomquist |
| 5,497,772 A | 3/1996 | Schulman et al. |
| 5,536,249 A | 7/1996 | Castellano et al. |
| 5,551,850 A | 9/1996 | Williamson et al. |
| 5,558,638 A | 9/1996 | Evers et al. |
| 5,569,186 A | 10/1996 | Lord et al. |
| 5,658,250 A | 8/1997 | Blomquist et al. |
| 5,658,252 A | 8/1997 | Johnson |
| 5,660,163 A | 8/1997 | Schulman et al. |
| 5,665,065 A | 9/1997 | Colman et al. |
| 5,669,877 A | 9/1997 | Blomquist |
| 5,674,240 A | 10/1997 | Bonutti et al. |
| 5,681,285 A | 10/1997 | Ford et al. |
| 5,685,844 A | 11/1997 | Marttila |
| 5,695,473 A | 12/1997 | Olsen |
| 5,712,856 A | 2/1998 | Eggers et al. |
| 5,745,378 A | 4/1998 | Barker et al. |
| 5,782,805 A | 7/1998 | Meinzer et al. |
| 5,810,771 A | 9/1998 | Blomquist |
| 5,814,015 A | 9/1998 | Gargano et al. |
| 5,822,715 A | 10/1998 | Worthington et al. |
| 5,876,370 A | 3/1999 | Blomquist |
| 5,879,143 A | 3/1999 | Cote et al. |
| 5,885,211 A | 3/1999 | Eppstein et al. |
| 5,919,216 A | 7/1999 | Houben et al. |
| 5,935,099 A | 8/1999 | Peterson et al. |
| 5,935,106 A | 8/1999 | Olsen |
| 5,960,403 A | 9/1999 | Brown |
| 6,023,629 A | 2/2000 | Tamada |
| 6,077,055 A | 9/2000 | Vilks |
| 6,122,536 A | 9/2000 | Sun et al. |
| 6,142,939 A | 11/2000 | Eppstein et al. |
| 6,175,752 B1 | 1/2001 | Say et al. |
| 6,232,130 B1 | 5/2001 | Wolf |
| 6,233,471 B1 | 5/2001 | Berner et al. |
| 6,241,704 B1 | 6/2001 | Peterson et al. |
| 6,248,057 B1 | 6/2001 | Mavity et al. |
| 6,248,065 B1 | 6/2001 | Brown |
| 6,248,067 B1 | 6/2001 | Causey, III et al. |
| 6,249,717 B1 | 6/2001 | Nicholson et al. |
| 6,255,781 B1 | 7/2001 | Tsumura |
| 6,272,364 B1 | 8/2001 | Kurnik |
| 6,298,254 B2 | 10/2001 | Tamada |
| 6,306,420 B1 | 10/2001 | Cheikh |
| 6,368,272 B1 | 4/2002 | Porumbescu |
| 6,379,301 B1 | 4/2002 | Worthington et al. |
| 6,422,057 B1 | 7/2002 | Anderson |
| 6,424,847 B1 | 7/2002 | Mastrototaro et al. |
| 6,475,180 B2 | 11/2002 | Peterson et al. |
| 6,475,750 B1 | 11/2002 | Han et al. |
| 6,505,059 B1 | 1/2003 | Kollias et al. |
| 6,517,482 B1 | 2/2003 | Elden et al. |
| 6,535,714 B2 | 3/2003 | Melker et al. |
| 6,539,250 B1 | 3/2003 | Bettinger |
| 6,544,212 B2 | 4/2003 | Galley et al. |
| 6,544,229 B1 | 4/2003 | Danby et al. |
| 6,546,269 B1 | 4/2003 | Kurnik |
| 6,551,276 B1 | 4/2003 | Mann et al. |
| 6,553,244 B2 | 4/2003 | Lesho et al. |
| 6,554,798 B1 | 4/2003 | Mann et al. |
| 6,558,320 B1 | 5/2003 | Causey, III et al. |
| 6,558,351 B1 | 5/2003 | Steil et al. |
| 6,562,001 B2 | 5/2003 | Lebel et al. |
| 6,565,509 B1 | 5/2003 | Say et al. |
| 6,571,128 B2 | 5/2003 | Lebel et al. |
| 6,572,542 B1 | 6/2003 | Houben et al. |
| 6,577,899 B2 | 6/2003 | Lebel et al. |
| 6,582,366 B1 | 6/2003 | Porumbescu |
| 6,595,919 B2 | 7/2003 | Berner et al. |
| 6,623,698 B2 | 9/2003 | Kuo |
| 6,635,014 B2 | 10/2003 | Starkweather et al. |
| 6,641,533 B2 | 11/2003 | Causey, III et al. |
| 6,648,821 B2 | 11/2003 | Lebel et al. |
| 6,650,951 B1 | 11/2003 | Jones et al. |
| 6,656,114 B1 | 12/2003 | Poulsen et al. |
| 6,659,978 B1 | 12/2003 | Kasuga et al. |
| 6,668,196 B1 | 12/2003 | Villegas et al. |
| 6,687,522 B2 | 2/2004 | Tamada |
| 6,692,456 B1 | 2/2004 | Eppstein et al. |
| 6,694,191 B2 | 2/2004 | Starkweather et al. |
| 6,740,072 B2 | 5/2004 | Starkweather et al. |
| 6,750,075 B2 | 5/2004 | Lebel et al. |
| 6,744,350 B2 | 6/2004 | Blomquist |
| 6,771,250 B1 | 8/2004 | Oh |
| 6,773,412 B2 | 8/2004 | O'Mahony et al. |
| 6,790,198 B1 | 9/2004 | White et al. |
| 6,809,563 B2 | 10/2004 | Schaal |
| 6,809,653 B1 | 10/2004 | Mann et al. |
| 6,810,290 B2 | 10/2004 | Lebel et al. |
| 6,827,702 B2 | 10/2004 | Lebel et al. |
| 6,835,175 B1 | 12/2004 | Porumbercu |
| 6,852,104 B2 | 2/2005 | Blomquist |

(56) References Cited

U.S. PATENT DOCUMENTS

| | | |
|---|---|---|
| 6,862,466 B2 | 3/2005 | Ackerman |
| 6,872,200 B2 | 3/2005 | Mann et al. |
| 6,873,268 B2 | 3/2005 | Lebel et al. |
| 6,880,564 B2 | 4/2005 | Erickson |
| 6,882,940 B2 | 4/2005 | Potts et al. |
| 6,895,263 B2 | 5/2005 | Shin et al. |
| 6,902,905 B2 | 6/2005 | Burson et al. |
| 6,916,159 B2 | 7/2005 | Rush et al. |
| 6,918,542 B2 | 7/2005 | Silverbrook et al. |
| 6,924,539 B2 | 8/2005 | Sharma |
| 6,934,220 B1 | 8/2005 | Cruitt et al. |
| 6,936,029 B2 | 8/2005 | Mann et al. |
| 6,957,655 B2 | 10/2005 | Erickson et al. |
| 6,958,705 B2 | 10/2005 | Lebel et al. |
| 6,966,325 B2 | 11/2005 | Erickson |
| 6,970,742 B2 | 11/2005 | Mann et al. |
| 6,974,437 B2 | 12/2005 | Lebel et al. |
| 6,979,326 B2 | 12/2005 | Mann et al. |
| 6,997,920 B2 | 2/2006 | Mann et al. |
| 6,998,387 B1 | 2/2006 | Goke et al. |
| 6,999,854 B2 | 2/2006 | Roth |
| 7,004,928 B2 | 2/2006 | Aceti et al. |
| 7,011,630 B2 | 3/2006 | Desai et al. |
| 7,022,072 B2 | 4/2006 | Fox et al. |
| 7,024,236 B2 | 4/2006 | Ford et al. |
| 7,025,743 B2 | 4/2006 | Mann et al. |
| 7,033,338 B2 | 4/2006 | Vilks et al. |
| 7,041,082 B2 | 5/2006 | Blomquist et al. |
| 7,073,713 B2 | 7/2006 | Silverbrook et al. |
| 7,083,108 B2 | 8/2006 | Silverbrook et al. |
| 7,092,011 B2 | 8/2006 | Silverbrook et al. |
| 7,097,104 B2 | 8/2006 | Silverbrook et al. |
| 7,097,108 B2 | 8/2006 | Zellner et al. |
| 7,098,803 B2 | 8/2006 | Mann et al. |
| 7,109,878 B2 | 9/2006 | Mann et al. |
| 7,150,741 B2 | 12/2006 | Erickson et al. |
| 7,156,808 B2 | 1/2007 | Quy |
| 7,179,226 B2 | 2/2007 | Crothall et al. |
| 7,181,505 B2 | 2/2007 | Haller et al. |
| 7,183,068 B2 | 2/2007 | Burson et al. |
| 7,187,404 B2 | 3/2007 | Silverbrook et al. |
| 7,201,319 B2 | 4/2007 | Silverbrook et al. |
| 7,204,823 B2 | 4/2007 | Estes et al. |
| 7,231,263 B2 | 6/2007 | Choi |
| 7,234,645 B2 | 6/2007 | Silverbrook et al. |
| 7,247,702 B2 | 7/2007 | Gardner et al. |
| 7,251,516 B2 | 7/2007 | Walker et al. |
| 7,254,782 B1 | 8/2007 | Sherer |
| 7,267,665 B2 | 9/2007 | Steil et al. |
| 7,278,983 B2 | 10/2007 | Ireland et al. |
| 7,282,029 B1 | 10/2007 | Poulsen et al. |
| 7,289,142 B2 | 10/2007 | Silverbrook |
| 7,291,107 B2 | 11/2007 | Hellwig et al. |
| 7,295,867 B2 | 11/2007 | Berner et al. |
| 7,307,245 B2 | 12/2007 | Faries, Jr. et al. |
| 7,320,675 B2 | 1/2008 | Pastore et al. |
| 7,324,012 B2 | 1/2008 | Mann et al. |
| 7,341,577 B2 | 3/2008 | Gill |
| 7,347,836 B2 | 3/2008 | Peterson et al. |
| 7,354,420 B2 | 4/2008 | Steil et al. |
| 7,362,971 B2 | 4/2008 | Silverbrook et al. |
| 7,373,083 B2 | 5/2008 | Silverbrook et al. |
| 7,377,706 B2 | 5/2008 | Silverbrook et al. |
| 7,399,277 B2 | 7/2008 | Saidara et al. |
| 7,402,153 B2 | 7/2008 | Steil et al. |
| 7,404,796 B2 | 7/2008 | Ginsberg |
| 7,440,806 B1 | 10/2008 | Whitehurst et al. |
| 7,446,091 B2 | 11/2008 | Van Den Berghe |
| 7,464,010 B2 | 12/2008 | Silverbrook et al. |
| 7,471,994 B2 | 12/2008 | Ford et al. |
| 7,475,825 B2 | 1/2009 | Silverbrook et al. |
| 7,483,050 B2 | 1/2009 | Silverbrook et al. |
| 7,483,743 B2 | 1/2009 | Mann et al. |
| 7,491,187 B2 | 2/2009 | Van Den Berghe et al. |
| 7,497,827 B2 | 3/2009 | Brister et al. |
| 7,515,060 B2 | 4/2009 | Blomquist |
| 7,524,045 B2 | 4/2009 | Silverbrook et al. |
| 7,534,226 B2 | 5/2009 | Mernoe et al. |
| 7,547,281 B2 | 6/2009 | Hellwig et al. |
| 7,556,613 B2 | 7/2009 | Wittman et al. |
| 7,559,926 B1 | 7/2009 | Blischak |
| 7,569,030 B2 | 8/2009 | Lebel et al. |
| 7,572,789 B2 | 8/2009 | Cowen et al. |
| 7,588,046 B1 | 9/2009 | Erickson |
| 7,591,801 B2 | 9/2009 | Brauker et al. |
| 7,602,310 B2 | 10/2009 | Mann et al. |
| 7,604,593 B2 | 10/2009 | Parris et al. |
| 7,615,007 B2 | 11/2009 | Shults et al. |
| 7,647,237 B2 | 1/2010 | Malave et al. |
| 7,651,489 B2 | 1/2010 | Estes et al. |
| 7,651,845 B2 | 1/2010 | Doyle, III et al. |
| 7,654,976 B2 | 2/2010 | Peterson et al. |
| 7,674,485 B2 | 3/2010 | Bhaskaran et al. |
| 7,676,519 B2 | 3/2010 | McBride et al. |
| 7,678,071 B2 | 3/2010 | Lebel et al. |
| 7,678,762 B2 | 3/2010 | Green et al. |
| 7,678,763 B2 | 3/2010 | Green et al. |
| 7,687,272 B1 | 3/2010 | Buchwald et al. |
| 7,697,967 B2 | 4/2010 | Stafford |
| 7,699,775 B2 | 4/2010 | Desai et al. |
| 7,704,226 B2 | 4/2010 | Mueller, Jr. et al. |
| 7,708,717 B2 | 5/2010 | Estes et al. |
| 7,711,402 B2 | 5/2010 | Shults et al. |
| 7,713,574 B2 | 5/2010 | Brister et al. |
| 7,715,893 B2 | 5/2010 | Kamath et al. |
| 7,717,903 B2 | 5/2010 | Estes et al. |
| 7,722,536 B2 | 5/2010 | Goodnow |
| 7,734,323 B2 | 6/2010 | Blomquist et al. |
| 7,751,907 B2 | 7/2010 | Blomquist |
| 7,766,829 B2 | 8/2010 | Sloan et al. |
| 7,766,830 B2 | 8/2010 | Fox et al. |
| 7,768,386 B2 | 8/2010 | Hayter et al. |
| 7,768,408 B2 | 8/2010 | Reggiardo et al. |
| 7,774,145 B2 | 8/2010 | Brauker et al. |
| 7,775,975 B2 | 8/2010 | Brister et al. |
| 7,776,030 B2 | 8/2010 | Estes et al. |
| 7,778,680 B2 | 8/2010 | Goode, Jr. et al. |
| 7,785,313 B2 | 8/2010 | Mastrototaro |
| 7,794,426 B2 | 9/2010 | Briones et al. |
| 7,794,427 B2 | 9/2010 | Estes et al. |
| 7,794,428 B2 | 9/2010 | Estes et al. |
| 7,797,028 B2 | 9/2010 | Goode, Jr. et al. |
| 7,801,582 B2 | 9/2010 | Peyser |
| 7,806,853 B2 | 10/2010 | Wittman et al. |
| 7,806,854 B2 | 10/2010 | Damiano et al. |
| 7,806,886 B2 | 10/2010 | Kanderian, Jr. et al. |
| 7,811,231 B2 | 10/2010 | Jin et al. |
| 7,811,455 B2 | 10/2010 | Hoss et al. |
| 7,815,602 B2 | 10/2010 | Mann et al. |
| 7,819,843 B2 | 10/2010 | Mann et al. |
| 7,826,879 B2 | 11/2010 | Hoss et al. |
| 7,828,528 B2 | 11/2010 | Estes et al. |
| 7,831,310 B2 | 11/2010 | Lebel et al. |
| 7,833,196 B2 | 11/2010 | Estes et al. |
| 7,837,647 B2 | 11/2010 | Estes et al. |
| 7,837,651 B2 | 11/2010 | Bishop et al. |
| 7,850,641 B2 | 12/2010 | Lebel et al. |
| 7,860,544 B2 | 12/2010 | Say et al. |
| 7,869,851 B2 | 1/2011 | Hellwig et al. |
| 7,869,853 B1 | 1/2011 | Say et al. |
| 7,875,922 B2 | 1/2011 | Wenger et al. |
| 7,884,729 B2 | 2/2011 | Reggiardo et al. |
| 7,885,699 B2 | 2/2011 | Say et al. |
| 7,887,512 B2 | 2/2011 | Estes et al. |
| 7,890,295 B2 | 2/2011 | Shin et al. |
| 7,892,199 B2 | 2/2011 | Mhatre et al. |
| 7,901,394 B2 | 3/2011 | Ireland et al. |
| 7,912,674 B2 | 3/2011 | Killoren Clark et al. |
| 7,914,450 B2 | 3/2011 | Goode et al. |
| 7,914,499 B2 | 3/2011 | Gonnelli et al. |
| 7,920,907 B2 | 4/2011 | McGarraugh et al. |
| 7,933,780 B2 | 4/2011 | De La Huerga |
| 7,935,076 B2 | 5/2011 | Estes et al. |
| 7,938,797 B2 | 5/2011 | Estes |

(56) References Cited

U.S. PATENT DOCUMENTS

| | | |
|---|---|---|
| 7,938,803 B2 | 5/2011 | Mernoe et al. |
| 7,941,200 B2 | 5/2011 | Weinert |
| 7,942,844 B2 | 5/2011 | Moberg et al. |
| 7,946,985 B2 | 5/2011 | Mastrototaro et al. |
| 7,951,114 B2 | 5/2011 | Rush et al. |
| 7,959,598 B2 | 6/2011 | Estes |
| 7,963,946 B2 | 6/2011 | Moubayed et al. |
| 7,967,773 B2 | 6/2011 | Amborn et al. |
| 7,972,296 B2 | 7/2011 | Braig et al. |
| 7,976,492 B2 | 7/2011 | Brauker et al. |
| 7,981,034 B2 | 7/2011 | Jennewine et al. |
| 7,981,084 B2 | 7/2011 | Estes et al. |
| 7,981,102 B2 | 7/2011 | Patel et al. |
| 7,983,745 B2 | 7/2011 | Hatlestad et al. |
| 7,983,759 B2 | 7/2011 | Stahmann et al. |
| 7,985,330 B2 | 7/2011 | Wang et al. |
| 7,988,630 B1 | 8/2011 | Osorio et al. |
| 7,988,849 B2 | 8/2011 | Biewer et al. |
| 7,996,158 B2 | 8/2011 | Hayter et al. |
| 8,000,763 B2 | 8/2011 | Mazza et al. |
| 8,005,524 B2 | 8/2011 | Brauker et al. |
| 8,012,119 B2 | 9/2011 | Estes et al. |
| 8,016,783 B2 | 9/2011 | Pastore et al. |
| 8,025,634 B1 | 9/2011 | Moubayed et al. |
| 8,029,443 B2 | 10/2011 | Goodnow |
| 8,029,459 B2 | 10/2011 | Rush et al. |
| 8,029,460 B2 | 10/2011 | Rush et al. |
| 8,062,249 B2 | 11/2011 | Wilinska et al. |
| 8,066,665 B2 | 11/2011 | Rush et al. |
| 8,075,527 B2 | 12/2011 | Rush et al. |
| 8,079,983 B2 | 12/2011 | Rush et al. |
| 8,079,984 B2 | 12/2011 | Rush et al. |
| 8,083,718 B2 | 12/2011 | Rush et al. |
| 8,088,098 B2 | 1/2012 | Yodfat et al. |
| 8,090,435 B2 | 1/2012 | Gill et al. |
| 8,093,212 B2 | 1/2012 | Gardner et al. |
| 8,105,268 B2 | 1/2012 | Lebel et al. |
| 8,105,279 B2 | 1/2012 | Mernoe et al. |
| 8,109,921 B2 | 2/2012 | Estes et al. |
| 8,114,350 B1 | 2/2012 | Silver et al. |
| 8,118,770 B2 | 2/2012 | Galley et al. |
| 8,119,593 B2 | 2/2012 | Richardson et al. |
| 8,121,857 B2 | 2/2012 | Galasso et al. |
| 8,127,046 B2 | 2/2012 | Grant et al. |
| 8,129,429 B2 | 3/2012 | Sporn et al. |
| 8,133,197 B2 | 3/2012 | Blomquist et al. |
| 8,140,275 B2 | 3/2012 | Campbell et al. |
| 8,140,312 B2 | 3/2012 | Hayter et al. |
| RE43,316 E | 4/2012 | Brown et al. |
| 8,147,446 B2 | 4/2012 | Yodfat et al. |
| 8,152,789 B2 | 4/2012 | Starkweather et al. |
| 8,323,188 B2 | 4/2012 | Tran |
| 8,170,721 B2 | 5/2012 | Nickerson |
| 8,177,716 B2 | 5/2012 | Say et al. |
| 8,182,445 B2 | 5/2012 | Moubayed et al. |
| 8,187,183 B2 | 5/2012 | Jin et al. |
| 8,192,394 B2 | 6/2012 | Ester et al. |
| 8,192,395 B2 | 6/2012 | Estes et al. |
| 8,202,267 B2 | 6/2012 | Field et al. |
| 8,204,729 B2 | 6/2012 | Sher |
| 8,206,296 B2 | 6/2012 | Jennewine |
| 8,206,350 B2 | 6/2012 | Mann et al. |
| 8,208,984 B2 | 6/2012 | Blomquist et al. |
| 8,211,062 B2 | 7/2012 | Estes et al. |
| 8,219,222 B2 | 7/2012 | Blomquist |
| 8,221,345 B2 | 7/2012 | Blomquist |
| 8,221,385 B2 | 7/2012 | Estes |
| 8,226,558 B2 | 7/2012 | Say et al. |
| 8,226,891 B2 | 7/2012 | Sloan et al. |
| 8,231,562 B2 | 7/2012 | Buck et al. |
| 8,234,126 B1 | 7/2012 | Estes |
| 8,234,128 B2 | 7/2012 | Martucci et al. |
| 8,237,715 B2 | 8/2012 | Buck et al. |
| 8,246,540 B2 | 8/2012 | Ginsberg |
| 8,250,483 B2 | 8/2012 | Blomquist |
| 8,251,904 B2 | 8/2012 | Zivitz et al. |
| 8,251,906 B2 | 8/2012 | Brauker et al. |
| 8,257,259 B2 | 9/2012 | Brauker et al. |
| 8,257,300 B2 | 9/2012 | Budiman et al. |
| 8,260,630 B2 | 9/2012 | Brown |
| 8,262,617 B2 | 9/2012 | Aeschlimann et al. |
| 8,275,438 B2 | 9/2012 | Simpson et al. |
| 8,277,435 B2 | 10/2012 | Estes |
| 8,282,601 B2 | 10/2012 | Mernoe et al. |
| 8,287,454 B2 | 10/2012 | Wolpert et al. |
| 8,287,487 B2 | 10/2012 | Estes |
| 8,287,495 B2 | 10/2012 | Michaud et al. |
| 8,287,514 B2 | 10/2012 | Miller et al. |
| 8,290,562 B2 | 10/2012 | Goode, Jr. et al. |
| 8,298,184 B2 | 10/2012 | Diperna et al. |
| 8,308,680 B1 | 11/2012 | Chawla |
| 8,311,749 B2 | 11/2012 | Brauker et al. |
| 8,326,546 B2 | 12/2012 | Stewart et al. |
| 8,328,754 B2 | 12/2012 | Estes et al. |
| 8,343,092 B2 | 1/2013 | Rush et al. |
| 8,344,847 B2 | 1/2013 | Moberg et al. |
| 8,346,399 B2 | 1/2013 | Blomquist |
| 8,348,885 B2 | 1/2013 | Moberg et al. |
| 8,348,886 B2 | 1/2013 | Kaderian et al. |
| 8,348,923 B2 | 1/2013 | Kanderian et al. |
| 8,349,319 B2 | 1/2013 | Schuchman et al. |
| 8,353,881 B2 | 1/2013 | Jennewine |
| 8,357,091 B2 | 1/2013 | Say et al. |
| 8,369,919 B2 | 2/2013 | Kamath et al. |
| 8,372,040 B2 | 2/2013 | Huang et al. |
| 8,376,943 B2 | 2/2013 | Kovach et al. |
| 8,377,031 B2 | 2/2013 | Hayter et al. |
| 8,380,273 B2 | 2/2013 | Say et al. |
| 8,409,131 B2 | 4/2013 | Say et al. |
| 8,414,523 B2 | 4/2013 | Blomquist et al. |
| 8,414,532 B2 | 4/2013 | Brandt et al. |
| 8,444,595 B2 | 5/2013 | Brukalo et al. |
| 8,449,523 B2 | 5/2013 | Brukalo et al. |
| 8,449,524 B2 | 5/2013 | Braig et al. |
| 8,451,230 B2 | 5/2013 | Celentano et al. |
| 8,452,953 B2 | 5/2013 | Buck et al. |
| 8,454,510 B2 | 6/2013 | Yodfat et al. |
| 8,454,575 B2 | 6/2013 | Estes et al. |
| 8,454,576 B2 | 6/2013 | Mastrototaro et al. |
| 8,454,581 B2 | 6/2013 | Estes et al. |
| 8,460,231 B2 | 6/2013 | Brauker et al. |
| 8,465,460 B2 | 6/2013 | Yodfat et al. |
| 8,467,980 B2 | 6/2013 | Campbell et al. |
| 8,486,005 B2 | 7/2013 | Yodfat et al. |
| 8,552,880 B2 | 10/2013 | Kopp et al. |
| 8,562,558 B2 | 10/2013 | Kamath et al. |
| 8,573,027 B2 | 11/2013 | Rosinko et al. |
| 8,579,853 B2 | 11/2013 | Reggiardo et al. |
| 8,650,937 B2 | 2/2014 | Brown |
| 8,657,779 B2 | 2/2014 | Blomquist |
| 8,706,691 B2 | 4/2014 | McDaniel et al. |
| 8,712,748 B2 | 4/2014 | Thukral et al. |
| 8,718,949 B2 | 5/2014 | Blomquist et al. |
| 8,726,266 B2 | 5/2014 | Kiaie et al. |
| 8,775,877 B2 | 7/2014 | McVey et al. |
| 8,801,657 B2 | 8/2014 | Blomquist et al. |
| 8,852,152 B2 | 10/2014 | Tverskoy |
| 8,882,701 B2 | 11/2014 | Debelser et al. |
| 8,926,561 B2 | 1/2015 | Verhoef |
| 8,932,250 B2 | 1/2015 | Montgomery |
| 8,936,565 B2 | 1/2015 | Chawla |
| 8,961,465 B2 | 2/2015 | Blomquist |
| 8,985,253 B2 | 3/2015 | Winter et al. |
| 8,986,253 B2 | 3/2015 | Diperna |
| 8,992,475 B2 | 3/2015 | Mann |
| 9,008,803 B2 | 4/2015 | Blomquist |
| 9,037,254 B2 | 5/2015 | John |
| 9,049,982 B2 | 6/2015 | Brukalo |
| 9,089,305 B2 | 7/2015 | Hovorka |
| 9,114,210 B2 | 8/2015 | Estes |
| 9,132,227 B2 | 9/2015 | Bryant, Jr. |
| 9,364,679 B2 | 6/2016 | John |
| 9,474,856 B2 | 10/2016 | Blomquist |
| 9,483,615 B2 | 11/2016 | Roberts |

(56) References Cited

U.S. PATENT DOCUMENTS

| | | |
|---|---|---|
| 9,486,171 B2 | 11/2016 | Saint |
| 9,486,578 B2 | 11/2016 | Finan et al. |
| 9,492,608 B2 | 11/2016 | Saint |
| 9,669,160 B2 | 6/2017 | Harris et al. |
| 9,833,177 B2 * | 12/2017 | Blomquist ............ G16H 20/17 |
| 9,867,937 B2 | 1/2018 | Saint et al. |
| 9,867,953 B2 | 1/2018 | Rosinko |
| 9,968,302 B2 | 5/2018 | Fennell |
| 9,968,306 B2 | 5/2018 | Cole |
| 9,968,729 B2 | 5/2018 | Estes |
| 9,974,472 B2 | 5/2018 | Hayter et al. |
| 9,974,903 B1 | 5/2018 | Davis |
| 10,016,559 B2 | 7/2018 | Debelser et al. |
| 10,016,561 B2 | 7/2018 | Saint et al. |
| 10,052,049 B2 | 8/2018 | Blomquist et al. |
| 10,207,047 B2 | 2/2019 | Estes |
| 10,213,547 B2 | 2/2019 | Rosinko |
| 10,357,606 B2 | 7/2019 | Rosinko et al. |
| 10,357,607 B2 | 7/2019 | Blomquist et al. |
| 2001/0001144 A1 | 5/2001 | Kapp |
| 2001/0027791 A1 | 10/2001 | Wallace et al. |
| 2001/0031944 A1 | 10/2001 | Peterson et al. |
| 2001/0037217 A1 | 11/2001 | Abensour et al. |
| 2001/0041831 A1 | 11/2001 | Starkweather et al. |
| 2002/0002326 A1 | 1/2002 | Causey, III et al. |
| 2002/0016568 A1 | 2/2002 | Lebel et al. |
| 2002/0065454 A1 | 5/2002 | Lebel et al. |
| 2002/0072932 A1 | 6/2002 | Swamy |
| 2002/0077852 A1 | 6/2002 | Ford et al. |
| 2002/0107476 A1 | 8/2002 | Mann et al. |
| 2002/0143580 A1 | 10/2002 | Bristol et al. |
| 2002/0183693 A1 | 12/2002 | Peterson et al. |
| 2002/0193679 A1 | 12/2002 | Malave et al. |
| 2003/0028089 A1 | 2/2003 | Galley et al. |
| 2003/0032867 A1 | 2/2003 | Crothall et al. |
| 2003/0036683 A1 | 2/2003 | Kehr et al. |
| 2003/0050621 A1 | 3/2003 | Lebel et al. |
| 2003/0055323 A1 | 3/2003 | Choi |
| 2003/0060765 A1 | 3/2003 | Campbell et al. |
| 2003/0065308 A1 | 4/2003 | Lebel et al. |
| 2003/0088238 A1 | 5/2003 | Poulsen et al. |
| 2003/0104982 A1 | 6/2003 | Wittmann et al. |
| 2003/0114836 A1 | 6/2003 | Estes et al. |
| 2003/0120616 A1 | 7/2003 | Steil et al. |
| 2003/0125612 A1 | 7/2003 | Fox et al. |
| 2003/0145854 A1 | 8/2003 | Hickle |
| 2003/0159945 A1 | 8/2003 | Miyazaki et al. |
| 2003/0160683 A1 | 8/2003 | Blomquist |
| 2003/0161744 A1 | 8/2003 | Vilks et al. |
| 2003/0163088 A1 | 8/2003 | Blomquist |
| 2003/0163090 A1 | 8/2003 | Blomquist et al. |
| 2003/0163223 A1 | 8/2003 | Blomquist |
| 2003/0163789 A1 | 8/2003 | Blomquist |
| 2003/0199854 A1 | 10/2003 | Kovach et al. |
| 2003/0208113 A1 | 11/2003 | Mault et al. |
| 2003/0211617 A1 | 11/2003 | Jones |
| 2003/0212364 A1 | 11/2003 | Mann et al. |
| 2003/0212379 A1 | 11/2003 | Bylund et al. |
| 2003/0236489 A1 | 12/2003 | Jacobson et al. |
| 2004/0015102 A1 | 1/2004 | Cummings et al. |
| 2004/0015132 A1 | 1/2004 | Brown |
| 2004/0054263 A1 | 3/2004 | Moerman et al. |
| 2004/0068230 A1 | 4/2004 | Estes et al. |
| 2004/0073095 A1 | 4/2004 | Causey, III et al. |
| 2004/0115067 A1 | 6/2004 | Rush et al. |
| 2004/0122353 A1 | 6/2004 | Shahmirian et al. |
| 2004/0152622 A1 | 8/2004 | Keith et al. |
| 2004/0167464 A1 | 8/2004 | Ireland et al. |
| 2004/0180810 A1 | 9/2004 | Pilarski |
| 2004/0193025 A1 | 9/2004 | Steil et al. |
| 2004/0193090 A1 | 9/2004 | Lebel et al. |
| 2004/0199409 A1 | 10/2004 | Brown |
| 2004/0220517 A1 | 11/2004 | Starkweather et al. |
| 2004/0225252 A1 | 11/2004 | Gillespie et al. |
| 2004/0254434 A1 | 12/2004 | Goodnow et al. |
| 2005/0017151 A1 | 1/2005 | Battig |
| 2005/0019755 A1 | 1/2005 | Marchessault et al. |
| 2005/0021006 A1 | 1/2005 | Tonnies |
| 2005/0022274 A1 | 1/2005 | Campbell et al. |
| 2005/0027182 A1 | 2/2005 | Siddiqui et al. |
| 2005/0030164 A1 | 2/2005 | Blomquist |
| 2005/0038332 A1 * | 2/2005 | Saidara ................ G16H 40/67 128/920 |
| 2005/0020621 A1 | 3/2005 | Thomas |
| 2005/0049179 A1 | 3/2005 | Davidson et al. |
| 2005/0065464 A1 | 3/2005 | Talbot et al. |
| 2005/0065750 A1 | 3/2005 | Murtfeldt et al. |
| 2005/0081847 A1 | 4/2005 | Lee et al. |
| 2005/0095063 A1 | 5/2005 | Fathallah et al. |
| 2005/0137530 A1 | 6/2005 | Campbell et al. |
| 2005/0143864 A1 | 6/2005 | Blomquist |
| 2005/0159656 A1 | 7/2005 | Hockersmith et al. |
| 2005/0171503 A1 | 8/2005 | Van Den Berghe et al. |
| 2005/0171513 A1 | 8/2005 | Mann et al. |
| 2005/0182358 A1 | 8/2005 | Veit et al. |
| 2005/0192557 A1 | 9/2005 | Brauker et al. |
| 2005/0197553 A1 | 9/2005 | Cooper |
| 2005/0197621 A1 | 9/2005 | Poulsen et al. |
| 2005/0203349 A1 | 9/2005 | Nanikashvili |
| 2005/0203360 A1 | 9/2005 | Brauker et al. |
| 2005/0228234 A1 | 10/2005 | Yang |
| 2005/0272640 A1 | 12/2005 | Doyle, III et al. |
| 2005/0277872 A1 | 12/2005 | Colby, Jr. et al. |
| 2005/0277912 A1 | 12/2005 | John |
| 2006/0001538 A1 | 1/2006 | Kraft et al. |
| 2006/0001550 A1 | 1/2006 | Mann et al. |
| 2006/0009727 A1 | 1/2006 | O'Mahony et al. |
| 2006/0010098 A1 | 1/2006 | Goodnow et al. |
| 2006/0014670 A1 | 1/2006 | Green et al. |
| 2006/0031094 A1 | 2/2006 | Cohen et al. |
| 2006/0047192 A1 | 3/2006 | Hellwig et al. |
| 2006/0047538 A1 | 3/2006 | Condurso et al. |
| 2006/0060765 A1 | 3/2006 | Huang |
| 2006/0085223 A1 | 4/2006 | Stupp et al. |
| 2006/0093785 A1 | 5/2006 | Hickle |
| 2006/0094985 A1 | 5/2006 | Aceti et al. |
| 2006/0122577 A1 | 6/2006 | Poulsen et al. |
| 2006/0132292 A1 | 6/2006 | Blomquist |
| 2006/0137695 A1 | 6/2006 | Hellwig et al. |
| 2006/0167345 A1 | 7/2006 | Vespasiani |
| 2006/0173406 A1 | 8/2006 | Hayes et al. |
| 2006/0173444 A1 | 8/2006 | Choy et al. |
| 2006/0202859 A1 | 9/2006 | Mastrototaro et al. |
| 2006/0224109 A1 | 10/2006 | Steil et al. |
| 2006/0253097 A1 | 11/2006 | Braig et al. |
| 2006/0253296 A1 | 11/2006 | Liisberg et al. |
| 2006/0264895 A1 | 11/2006 | Flanders |
| 2006/0271020 A1 | 11/2006 | Huang et al. |
| 2006/0272652 A1 | 12/2006 | Stocker et al. |
| 2006/0276771 A1 | 12/2006 | Galley et al. |
| 2007/0010950 A1 | 1/2007 | Abensour et al. |
| 2007/0016127 A1 | 1/2007 | Staib et al. |
| 2007/0016170 A1 | 1/2007 | Kovelman |
| 2007/0016449 A1 | 1/2007 | Cohen et al. |
| 2007/0021733 A1 | 1/2007 | Hansen et al. |
| 2007/0033074 A1 | 2/2007 | Nitzan et al. |
| 2007/0060796 A1 | 3/2007 | Kim |
| 2007/0060871 A1 | 3/2007 | Istoc et al. |
| 2007/0060874 A1 | 3/2007 | Nesbitt et al. |
| 2007/0066956 A1 | 3/2007 | Finkel |
| 2007/0073236 A1 | 3/2007 | Mernoe et al. |
| 2007/0078314 A1 | 4/2007 | Grounsell et al. |
| 2007/0083152 A1 | 4/2007 | Williams, Jr. et al. |
| 2007/0083335 A1 | 4/2007 | Moerman |
| 2007/0093786 A1 | 4/2007 | Goldsmith et al. |
| 2007/0100222 A1 | 5/2007 | Mastrototaro et al. |
| 2007/0106135 A1 * | 5/2007 | Sloan ................... G16H 10/40 604/65 |
| 2007/0112261 A1 | 5/2007 | Enegren et al. |
| 2007/0112298 A1 | 5/2007 | Mueller, Jr. et al. |
| 2007/0112299 A1 | 5/2007 | Smit et al. |
| 2007/0118405 A1 | 5/2007 | Campbell et al. |
| 2007/0124002 A1 | 5/2007 | Estes et al. |
| 2007/0149861 A1 | 6/2007 | Crothall et al. |

(56) References Cited

U.S. PATENT DOCUMENTS

| | | |
|---|---|---|
| 2007/0156033 A1 | 7/2007 | Causey, III et al. |
| 2007/0156092 A1 | 7/2007 | Estes et al. |
| 2007/0156457 A1 | 7/2007 | Brown |
| 2007/0167905 A1 | 7/2007 | Estes et al. |
| 2007/0167912 A1 | 7/2007 | Causey et al. |
| 2007/0173712 A1 | 7/2007 | Shah et al. |
| 2007/0173761 A1 | 7/2007 | Kanderian, Jr. et al. |
| 2007/0173762 A1 | 7/2007 | Estes et al. |
| 2007/0179355 A1 | 8/2007 | Rosen |
| 2007/0179444 A1 | 8/2007 | Causey et al. |
| 2007/0203454 A1 | 8/2007 | Shermer et al. |
| 2007/0213657 A1 | 9/2007 | Jennewine et al. |
| 2007/0233051 A1 | 10/2007 | Hohl et al. |
| 2007/0245258 A1 | 10/2007 | Ginggen et al. |
| 2007/0251835 A1 | 11/2007 | Mehta et al. |
| 2007/0253021 A1 | 11/2007 | Mehta et al. |
| 2007/0253380 A1 | 11/2007 | Jollota et al. |
| 2007/0254593 A1 | 11/2007 | Jollota et al. |
| 2007/0255116 A1 | 11/2007 | Mehta et al. |
| 2007/0255125 A1 | 11/2007 | Moberg et al. |
| 2007/0255126 A1 | 11/2007 | Moberg et al. |
| 2007/0255250 A1 | 11/2007 | Moberg et al. |
| 2007/0255348 A1 | 11/2007 | Holtzclaw |
| 2007/0258395 A1 | 11/2007 | Jollota et al. |
| 2007/0287985 A1 | 12/2007 | Estes et al. |
| 2007/0299389 A1 | 12/2007 | Halbert et al. |
| 2008/0004601 A1 | 1/2008 | Jennewine et al. |
| 2008/0017203 A1 | 1/2008 | Fagg et al. |
| 2008/0030369 A1 | 2/2008 | Mann et al. |
| 2008/0033357 A1 | 2/2008 | Mann et al. |
| 2008/0033360 A1 | 2/2008 | Evans et al. |
| 2008/0033361 A1 | 2/2008 | Evans et al. |
| 2008/0045902 A1 | 2/2008 | Estes et al. |
| 2008/0045903 A1 | 2/2008 | Estes et al. |
| 2008/0045904 A1 | 2/2008 | Estes et al. |
| 2008/0045931 A1 | 2/2008 | Estes et al. |
| 2008/0051709 A1 | 2/2008 | Mounce et al. |
| 2008/0051714 A1 | 2/2008 | Moberg et al. |
| 2008/0051716 A1 | 2/2008 | Stutz |
| 2008/0058773 A1 | 3/2008 | John |
| 2008/0065007 A1 | 3/2008 | Peterson et al. |
| 2008/0065016 A1 | 3/2008 | Peterson et al. |
| 2008/0071209 A1 | 3/2008 | Moubayed et al. |
| 2008/0071210 A1 | 3/2008 | Moubayed et al. |
| 2008/0071217 A1 | 3/2008 | Moubayed et al. |
| 2008/0071251 A1 | 3/2008 | Moubayed |
| 2008/0071580 A1 | 3/2008 | Marcus et al. |
| 2008/0076969 A1 | 3/2008 | Kraft et al. |
| 2008/0097289 A1 | 4/2008 | Steil et al. |
| 2008/0103447 A1 | 4/2008 | Reggiardo et al. |
| 2008/0106431 A1 | 5/2008 | Blomquist |
| 2008/0114299 A1 | 5/2008 | Damgaard-Sorensen et al. |
| 2008/0132844 A1 | 6/2008 | Peterson et al. |
| 2008/0139907 A1 | 6/2008 | Rao et al. |
| 2008/0139910 A1 | 6/2008 | Mastrototaro et al. |
| 2008/0147041 A1 | 6/2008 | Kristensen |
| 2008/0147042 A1 | 6/2008 | Pettis et al. |
| 2008/0147050 A1 | 6/2008 | Mann et al. |
| 2008/0147704 A1 | 6/2008 | Mann et al. |
| 2008/0154513 A1 | 6/2008 | Kovatchev et al. |
| 2008/0156661 A1 | 7/2008 | Cooper et al. |
| 2008/0171697 A1 | 7/2008 | Jacotot et al. |
| 2008/0171967 A1 | 7/2008 | Blomquist et al. |
| 2008/0172026 A1 | 7/2008 | Blomquist |
| 2008/0172028 A1 | 7/2008 | Blomquist |
| 2008/0172029 A1 | 7/2008 | Blomquist |
| 2008/0172030 A1 | 7/2008 | Blomquist |
| 2008/0172031 A1 | 7/2008 | Blomquist |
| 2008/0177165 A1 | 7/2008 | Blomquist et al. |
| 2008/0183060 A1 | 7/2008 | Steil et al. |
| 2008/0206799 A1 | 8/2008 | Blomquist |
| 2008/0222246 A1 | 9/2008 | Ebling et al. |
| 2008/0228055 A1 | 9/2008 | Sher |
| 2008/0228056 A1 | 9/2008 | Blomquist et al. |
| 2008/0249470 A1 | 10/2008 | Malave et al. |
| 2008/0255438 A1 | 10/2008 | Saidara et al. |
| 2008/0255517 A1 | 10/2008 | Nair et al. |
| 2008/0264024 A1 | 10/2008 | Baaken |
| 2008/0269585 A1 | 10/2008 | Ginsberg |
| 2008/0269714 A1 | 10/2008 | Mastrototaro et al. |
| 2008/0269723 A1 | 10/2008 | Mastrototaro et al. |
| 2008/0287922 A1 | 11/2008 | Panduro |
| 2008/0288115 A1 | 11/2008 | Rusnak et al. |
| 2008/0294024 A1 | 11/2008 | Cosentino et al. |
| 2008/0294094 A1 | 11/2008 | Mhatre et al. |
| 2008/0294108 A1 | 11/2008 | Briones et al. |
| 2008/0294109 A1 | 11/2008 | Estes et al. |
| 2008/0294142 A1 | 11/2008 | Patel et al. |
| 2008/0294294 A1 | 11/2008 | Blomquist |
| 2008/0300534 A1 | 12/2008 | Blomquist |
| 2008/0300572 A1 | 12/2008 | Rankers et al. |
| 2008/0300651 A1 | 12/2008 | Gerber et al. |
| 2008/0306353 A1 | 12/2008 | Douglas et al. |
| 2008/0306434 A1 | 12/2008 | Dobbles et al. |
| 2008/0306444 A1 | 12/2008 | Brister et al. |
| 2008/0312584 A1 | 12/2008 | Montgomery et al. |
| 2008/0312585 A1 | 12/2008 | Brukalo et al. |
| 2009/0005726 A1 | 1/2009 | Jones et al. |
| 2009/0006061 A1 | 1/2009 | Thukral et al. |
| 2009/0006129 A1 | 1/2009 | Thukral et al. |
| 2009/0018779 A1 | 1/2009 | Cohen et al. |
| 2009/0030733 A1 | 1/2009 | Cohen et al. |
| 2009/0036753 A1 | 2/2009 | King |
| 2009/0054475 A1 | 2/2009 | Chen et al. |
| 2009/0054750 A1 | 2/2009 | Jennewine |
| 2009/0067989 A1 | 3/2009 | Estes et al. |
| 2009/0069745 A1 | 3/2009 | Estes et al. |
| 2009/0069749 A1 | 3/2009 | Miller et al. |
| 2009/0069787 A1 | 3/2009 | Estes et al. |
| 2009/0085768 A1 | 4/2009 | Patel et al. |
| 2009/0088731 A1 | 4/2009 | Campbell et al. |
| 2009/0093756 A1 | 4/2009 | Minaie et al. |
| 2009/0105636 A1 | 4/2009 | Hayter et al. |
| 2009/0105646 A1 | 4/2009 | Hendrixson et al. |
| 2009/0112626 A1 | 4/2009 | Talbot et al. |
| 2009/0118592 A1 | 5/2009 | Klitgaard |
| 2009/0131860 A1 | 5/2009 | Nielson |
| 2009/0131861 A1 | 5/2009 | Braig et al. |
| 2009/0143661 A1 | 6/2009 | Taub et al. |
| 2009/0150186 A1 | 6/2009 | Cohen et al. |
| 2009/0150865 A1 | 6/2009 | Young et al. |
| 2009/0156990 A1 | 6/2009 | Wenger et al. |
| 2009/0157003 A1 | 6/2009 | Jones et al. |
| 2009/0163855 A1 | 6/2009 | Shin et al. |
| 2009/0164239 A1 | 6/2009 | Hayter et al. |
| 2009/0171269 A1 | 7/2009 | Jennewine et al. |
| 2009/0177142 A1 | 7/2009 | Blomquist et al. |
| 2009/0177147 A1 | 7/2009 | Blomquist et al. |
| 2009/0177154 A1 | 7/2009 | Blomquist |
| 2009/0177180 A1 | 7/2009 | Rubalcaba, Jr. et al. |
| 2009/0192366 A1 | 7/2009 | Mensinger et al. |
| 2009/0192724 A1 | 7/2009 | Brauker et al. |
| 2009/0192745 A1 | 7/2009 | Kamath et al. |
| 2009/0212966 A1 | 8/2009 | Panduro |
| 2009/0216100 A1 | 8/2009 | Ebner et al. |
| 2009/0221890 A1 | 9/2009 | Saffer et al. |
| 2009/0240193 A1 | 9/2009 | Mensinger et al. |
| 2009/0247931 A1 | 10/2009 | Damgaard-Sorensen |
| 2009/0247982 A1 | 10/2009 | Krulevitch et al. |
| 2009/0254037 A1 | 10/2009 | Bryant, Jr. et al. |
| 2009/0267774 A1 | 10/2009 | Enegren et al. |
| 2009/0267775 A1 | 10/2009 | Enegren et al. |
| 2009/0270705 A1 | 10/2009 | Enegren et al. |
| 2009/0270810 A1 | 10/2009 | Debelser et al. |
| 2009/0275886 A1 | 11/2009 | Blomquist et al. |
| 2009/0275887 A1 | 11/2009 | Estes |
| 2009/0281393 A1 | 11/2009 | Smith |
| 2010/0008795 A1 | 1/2010 | Diperna |
| 2010/0010330 A1 | 1/2010 | Rankers et al. |
| 2010/0030045 A1 | 2/2010 | Gottlieb et al. |
| 2010/0030387 A1 | 2/2010 | Sen |
| 2010/0049164 A1 | 2/2010 | Estes |
| 2010/0056993 A1 | 3/2010 | Chase |
| 2010/0057040 A1 | 3/2010 | Hayter |

(56) References Cited

U.S. PATENT DOCUMENTS

| | | |
|---|---|---|
| 2010/0057043 A1 | 3/2010 | Kovatchev et al. |
| 2010/0064257 A1 | 3/2010 | Buck et al. |
| 2010/0069730 A1 | 3/2010 | Bergstrom et al. |
| 2010/0081993 A1 | 4/2010 | O'Connor |
| 2010/0094110 A1 | 4/2010 | Heller et al. |
| 2010/0094251 A1 | 4/2010 | Estes |
| 2010/0095229 A1 | 4/2010 | Dixon et al. |
| 2010/0205999 A1 | 4/2010 | Dixon et al. |
| 2010/0114015 A1 | 5/2010 | Kanderian, Jr. et al. |
| 2010/0121169 A1 | 5/2010 | Petisce et al. |
| 2010/0121170 A1 | 5/2010 | Rule |
| 2010/0125241 A1 | 5/2010 | Prud et al. |
| 2010/0130933 A1 | 5/2010 | Holland et al. |
| 2010/0138197 A1 | 6/2010 | Sher |
| 2010/0145173 A1 | 6/2010 | Alferness et al. |
| 2010/0145276 A1 | 6/2010 | Yodfat et al. |
| 2010/0145303 A1 | 6/2010 | Yodfat et al. |
| 2010/0156633 A1 | 6/2010 | Buck, Jr. et al. |
| 2010/0160740 A1 | 6/2010 | Cohen et al. |
| 2010/0161236 A1 | 6/2010 | Cohen et al. |
| 2010/0161346 A1 | 6/2010 | Getschmann et al. |
| 2010/0162786 A1 | 7/2010 | Keenan et al. |
| 2010/0168538 A1 | 7/2010 | Keenan et al. |
| 2010/0174266 A1 | 7/2010 | Estes |
| 2010/0174553 A1 | 7/2010 | Kaufman et al. |
| 2010/0179402 A1 | 7/2010 | Goode, Jr. et al. |
| 2010/0185142 A1 | 7/2010 | Kamen et al. |
| 2010/0185152 A1 | 7/2010 | Larsen et al. |
| 2010/0185175 A1 | 7/2010 | Kamen et al. |
| 2010/0192686 A1 | 8/2010 | Kamen et al. |
| 2010/0198034 A1 | 8/2010 | Thomas et al. |
| 2010/0198142 A1 | 8/2010 | Sloan et al. |
| 2010/0202040 A1 | 8/2010 | Morgan |
| 2010/0205001 A1 | 8/2010 | Knudsen et al. |
| 2010/0218132 A1 | 8/2010 | Soni et al. |
| 2010/0222765 A1 | 9/2010 | Blomquist et al. |
| 2010/0228186 A1 | 9/2010 | Estes et al. |
| 2010/0234709 A1 | 9/2010 | Say et al. |
| 2010/0235439 A1 | 9/2010 | Goodnow |
| 2010/0249530 A1 | 9/2010 | Rankers et al. |
| 2010/0249561 A1 | 9/2010 | Patek et al. |
| 2010/0261987 A1 | 10/2010 | Kamath et al. |
| 2010/0262078 A1 | 10/2010 | Blomquist |
| 2010/0262117 A1 | 10/2010 | Magni et al. |
| 2010/0262434 A1 | 10/2010 | Shaya |
| 2010/0274218 A1 | 10/2010 | Yodfat et al. |
| 2010/0274592 A1 | 10/2010 | Nitzan et al. |
| 2010/0274751 A1 | 10/2010 | Blomquist |
| 2010/0277119 A1 | 11/2010 | Montague et al. |
| 2010/0280329 A1 | 11/2010 | Randloev et al. |
| 2010/0280442 A1 | 11/2010 | Shahmirian et al. |
| 2010/0286563 A1 | 11/2010 | Bryer et al. |
| 2010/0286601 A1 | 11/2010 | Yodfat et al. |
| 2010/0286653 A1 | 11/2010 | Kubel et al. |
| 2010/0292634 A1* | 11/2010 | Kircher, Jr. ............ G16H 20/13 604/66 |
| 2010/0295686 A1 | 11/2010 | Sloan et al. |
| 2010/0298681 A1 | 11/2010 | Say et al. |
| 2010/0298685 A1 | 11/2010 | Hayter et al. |
| 2010/0305421 A1 | 12/2010 | Ow-Wing |
| 2010/0305545 A1 | 12/2010 | Kanderian, Jr. et al. |
| 2010/0305965 A1 | 12/2010 | Benjamin et al. |
| 2010/0312085 A1 | 12/2010 | Andrews et al. |
| 2010/0317950 A1 | 12/2010 | Galley et al. |
| 2010/0317951 A1 | 12/2010 | Rutkowski et al. |
| 2010/0324382 A1 | 12/2010 | Cantwell et al. |
| 2010/0324398 A1 | 12/2010 | Tzyy-Ping |
| 2010/0331651 A1 | 12/2010 | Groll |
| 2011/0004188 A1 | 1/2011 | Shekalim |
| 2011/0006876 A1 | 1/2011 | Moberg et al. |
| 2011/0009725 A1 | 1/2011 | Hill et al. |
| 2011/0009813 A1 | 1/2011 | Rankers |
| 2011/0010105 A1 | 1/2011 | Shah et al. |
| 2011/0015509 A1 | 1/2011 | Peyser |
| 2011/0021898 A1 | 1/2011 | Wei et al. |
| 2011/0022025 A1 | 1/2011 | Savoie et al. |
| 2011/0033833 A1 | 2/2011 | Blomquist et al. |
| 2011/0034792 A1 | 2/2011 | Williams et al. |
| 2011/0040247 A1 | 2/2011 | Mandro et al. |
| 2011/0040251 A1 | 2/2011 | Blomquist et al. |
| 2011/0046051 A1 | 2/2011 | Moerman |
| 2011/0046892 A1 | 2/2011 | Moerman |
| 2011/0047499 A1 | 2/2011 | Mandro et al. |
| 2011/0048938 A1 | 3/2011 | Shah et al. |
| 2011/0048941 A1 | 3/2011 | Shah et al. |
| 2011/0050428 A1 | 3/2011 | Istoc |
| 2011/0053121 A1 | 3/2011 | Heaton |
| 2011/0054281 A1 | 3/2011 | Shah et al. |
| 2011/0054390 A1 | 3/2011 | Searle et al. |
| 2011/0054391 A1 | 3/2011 | Ward et al. |
| 2011/0056264 A1 | 3/2011 | Kaplan et al. |
| 2011/0058485 A1 | 3/2011 | Sloan |
| 2011/0060281 A1 | 3/2011 | Aeschlimann et al. |
| 2011/0071372 A1 | 3/2011 | Sloan et al. |
| 2011/0071464 A1 | 3/2011 | Palerm |
| 2011/0071465 A1 | 3/2011 | Wang et al. |
| 2011/0071765 A1 | 3/2011 | Yodfat et al. |
| 2011/0077481 A1 | 3/2011 | Say et al. |
| 2011/0077493 A1 | 3/2011 | Shadforth et al. |
| 2011/0077963 A1 | 3/2011 | Knudsen et al. |
| 2011/0082439 A1 | 4/2011 | Wenger et al. |
| 2011/0087165 A1 | 4/2011 | Amborn et al. |
| 2011/0092788 A1 | 4/2011 | Long et al. |
| 2011/0092894 A1 | 4/2011 | McGill et al. |
| 2011/0098548 A1 | 4/2011 | Budiman et al. |
| 2011/0098637 A1 | 4/2011 | Hill |
| 2011/0098638 A1 | 4/2011 | Chawla et al. |
| 2011/0098674 A1 | 4/2011 | Vicente et al. |
| 2011/0101995 A1 | 5/2011 | Shah et al. |
| 2011/0105873 A1 | 5/2011 | Feldman et al. |
| 2011/0105955 A1 | 5/2011 | Yudovsky et al. |
| 2011/0106011 A1 | 5/2011 | Cinar et al. |
| 2011/0106049 A1 | 5/2011 | Damiano et al. |
| 2011/0106050 A1 | 5/2011 | Yodfat et al. |
| 2011/0106480 A1 | 5/2011 | Shah et al. |
| 2011/0112504 A1 | 5/2011 | Causey et al. |
| 2011/0112505 A1 | 5/2011 | Starkweather et al. |
| 2011/0112506 A1 | 5/2011 | Starkweather et al. |
| 2011/0118578 A1 | 5/2011 | Timmerman |
| 2011/0118662 A1 | 5/2011 | Mhatre et al. |
| 2011/0118699 A1 | 5/2011 | Yodfat et al. |
| 2011/0124996 A1 | 5/2011 | Rienke et al. |
| 2011/0124999 A1 | 5/2011 | Reggiardo et al. |
| 2011/0125085 A1 | 5/2011 | McGill et al. |
| 2011/0125095 A1 | 5/2011 | Lebel et al. |
| 2011/0126188 A1 | 5/2011 | Bernstein et al. |
| 2011/0130716 A1 | 6/2011 | Estes et al. |
| 2011/0130746 A1 | 6/2011 | Budiman |
| 2011/0133946 A1 | 6/2011 | Kopp et al. |
| 2011/0137239 A1 | 6/2011 | Debelser et al. |
| 2011/0144586 A1 | 6/2011 | Michaud et al. |
| 2011/0144616 A1 | 6/2011 | Michaud et al. |
| 2011/0152770 A1 | 6/2011 | Diperna et al. |
| 2011/0152824 A1 | 6/2011 | Diperna et al. |
| 2011/0160654 A1 | 6/2011 | Hanson et al. |
| 2011/0160695 A1 | 6/2011 | Sigrist et al. |
| 2011/0163881 A1 | 7/2011 | Halff et al. |
| 2011/0166544 A1 | 7/2011 | Verhoef et al. |
| 2011/0166875 A1 | 7/2011 | Hayter et al. |
| 2011/0172744 A1 | 7/2011 | David et al. |
| 2011/0178461 A1 | 7/2011 | Chong et al. |
| 2011/0178462 A1 | 7/2011 | Moberg et al. |
| 2011/0178717 A1 | 7/2011 | Goodnow et al. |
| 2011/0184264 A1 | 7/2011 | Galasso et al. |
| 2011/0184342 A1 | 7/2011 | Pesach et al. |
| 2011/0190614 A1 | 8/2011 | Brister et al. |
| 2011/0190701 A1 | 8/2011 | Remde et al. |
| 2011/0193704 A1 | 8/2011 | Harper et al. |
| 2011/0196213 A1 | 8/2011 | Thukral et al. |
| 2011/0202040 A1 | 8/2011 | Remde et al. |
| 2011/0205065 A1 | 8/2011 | Strachan et al. |
| 2011/0208155 A1 | 8/2011 | Palerm et al. |
| 2011/0213225 A1 | 9/2011 | Bernstein et al. |
| 2011/0213306 A1 | 9/2011 | Hanson et al. |

(56) References Cited

U.S. PATENT DOCUMENTS

| | | |
|---|---|---|
| 2011/0238033 A1 | 9/2011 | Prod'Hom et al. |
| 2011/0256024 A1 | 10/2011 | Cole et al. |
| 2011/0257625 A1 | 10/2011 | Jasperson et al. |
| 2011/0257627 A1 | 10/2011 | Hovorka |
| 2011/0257895 A1 | 10/2011 | Brauker et al. |
| 2011/0266999 A1 | 11/2011 | Yodfat et al. |
| 2012/0013625 A1 | 1/2012 | Blomquist et al. |
| 2012/0013802 A1 | 1/2012 | Blomquist et al. |
| 2012/0029433 A1 | 2/2012 | Michaud et al. |
| 2012/0029468 A1 | 2/2012 | Diperna |
| 2012/0029941 A1 | 2/2012 | Malave et al. |
| 2012/0030610 A1 | 2/2012 | Diperna et al. |
| 2012/0041415 A1 | 2/2012 | Estes et al. |
| 2012/0053522 A1 | 3/2012 | Yodfat et al. |
| 2012/0059353 A1 | 3/2012 | Kovatchev et al. |
| 2012/0059673 A1 | 3/2012 | Cohen et al. |
| 2012/0095315 A1 | 4/2012 | Tenbarge et al. |
| 2012/0123230 A1 | 5/2012 | Brown et al. |
| 2012/0163481 A1 | 6/2012 | Ebner et al. |
| 2012/0185267 A1 | 7/2012 | Kamen et al. |
| 2012/0191061 A1 | 7/2012 | Yodfat et al. |
| 2012/0191063 A1 | 7/2012 | Brauker et al. |
| 2012/0203178 A1 | 8/2012 | Tverskoy |
| 2012/0226124 A1 | 9/2012 | Blomquist |
| 2012/0232484 A1 | 9/2012 | Blomquist |
| 2012/0232485 A1 | 9/2012 | Blomquist |
| 2012/0232520 A1 | 9/2012 | Sloan et al. |
| 2012/0232521 A1 | 9/2012 | Blomquist |
| 2012/0238852 A1 | 9/2012 | Brauker et al. |
| 2012/0238854 A1 | 9/2012 | Blomquist et al. |
| 2012/0239362 A1 | 9/2012 | Blomquist |
| 2012/0245524 A1 | 9/2012 | Estes et al. |
| 2012/0265722 A1 | 10/2012 | Blomquist |
| 2012/0296269 A1 | 11/2012 | Blomquist |
| 2012/0302991 A1 | 11/2012 | Blomquist et al. |
| 2012/0330227 A1 | 12/2012 | Budiman et al. |
| 2013/0005633 A1 | 1/2013 | Habeeb et al. |
| 2013/0012917 A1 | 1/2013 | Miller et al. |
| 2013/0046281 A1 | 2/2013 | Javitt |
| 2013/0053816 A1 | 2/2013 | Diperna et al. |
| 2013/0116649 A1 | 5/2013 | Breton |
| 2013/0131630 A1 | 5/2013 | Bloquist |
| 2013/0324824 A1 | 12/2013 | Kamath et al. |
| 2013/0324928 A1 | 12/2013 | Kruse |
| 2013/0331790 A1 | 12/2013 | Brown et al. |
| 2013/0345625 A1 | 12/2013 | Causey, III et al. |
| 2013/0345663 A1 | 12/2013 | Agrawal et al. |
| 2014/0012511 A1 | 1/2014 | Mensinger et al. |
| 2014/0019396 A1 | 1/2014 | Carlsgaard et al. |
| 2014/0066890 A1 | 3/2014 | Sloan et al. |
| 2014/0074059 A1 | 3/2014 | Howell et al. |
| 2014/0113553 A1 | 4/2014 | Brukalo |
| 2014/0137641 A1 | 5/2014 | Brown |
| 2014/0171772 A1 | 6/2014 | Blomquist |
| 2014/0180203 A1 | 6/2014 | Budiman |
| 2014/0200426 A1 | 7/2014 | Taub |
| 2014/0273042 A1 | 9/2014 | Saint |
| 2014/0275419 A1 | 9/2014 | Ward et al. |
| 2014/0276419 A1 | 9/2014 | Rosinko et al. |
| 2014/0276420 A1 | 9/2014 | Rosinko |
| 2014/0276531 A1 | 9/2014 | Walsh |
| 2014/0276553 A1 | 9/2014 | Rosinko et al. |
| 2014/0276556 A1 | 9/2014 | Saint et al. |
| 2014/0276570 A1 | 9/2014 | Saint |
| 2014/0276574 A1 | 9/2014 | Saint |
| 2014/0350371 A1 | 11/2014 | Blomquist et al. |
| 2014/0278898 A1 | 12/2014 | Rosinko |
| 2014/0374275 A1 | 12/2014 | Morales et al. |
| 2015/0045770 A1 | 2/2015 | Debelser et al. |
| 2015/0073337 A1 | 3/2015 | Saint et al. |
| 2015/0119805 A1 | 4/2015 | Blomquist |
| 2015/0157793 A1 | 6/2015 | Kovelman |
| 2015/0174320 A1 | 6/2015 | Grant et al. |
| 2015/0182693 A1 | 7/2015 | Rosinko |
| 2015/0182695 A1 | 7/2015 | Rosinko |
| 2015/0217044 A1 | 8/2015 | Blomquist |
| 2015/0273147 A1 | 10/2015 | Duke et al. |
| 2015/0314062 A1 | 11/2015 | Blomquist et al. |
| 2015/0352282 A1 | 12/2015 | Mazlish |
| 2016/0030669 A1 | 2/2016 | Harris et al. |
| 2016/0082188 A1 | 3/2016 | Blomquist et al. |
| 2016/0199571 A1 | 7/2016 | Rosinko et al. |
| 2016/0228041 A1 | 8/2016 | Heller et al. |
| 2017/0000943 A1 | 1/2017 | Blomquist et al. |
| 2017/0043085 A1 | 2/2017 | Rosinko |
| 2017/0182248 A1 | 6/2017 | Rosinko |
| 2018/0092578 A1 | 4/2018 | Blomquist |
| 2018/0093039 A1 | 4/2018 | Estes |
| 2018/0110921 A1 | 4/2018 | Saint et al. |
| 2018/0133397 A1 | 5/2018 | Estes |
| 2018/0137252 A1 | 5/2018 | Mairs et al. |
| 2018/0137938 A1 | 5/2018 | Vaddiraju et al. |
| 2018/0161498 A1 | 6/2018 | Estes |
| 2018/0193573 A1 | 7/2018 | Rosinko |
| 2018/0304010 A1 | 10/2018 | Debelser et al. |
| 2019/0022314 A1 | 1/2019 | Schmidt |
| 2019/0175823 A1 | 6/2019 | Rosinko |
| 2019/0328967 A1 | 10/2019 | Blomquist |

FOREIGN PATENT DOCUMENTS

| | | |
|---|---|---|
| DE | 19819407 A1 | 11/1999 |
| DE | 10121317 A1 | 11/2002 |
| DE | 10352456 A1 | 7/2005 |
| EP | 1102194 A2 | 5/2001 |
| EP | 1571582 A2 | 9/2005 |
| EP | 1500029 B1 | 4/2007 |
| JP | 2006034323 A | 2/2006 |
| JP | 22010503515 A | 2/2010 |
| WO | 0010628 | 3/2000 |
| WO | 0045696 A1 | 8/2000 |
| WO | 0074753 A1 | 12/2000 |
| WO | 0152727 A1 | 7/2001 |
| WO | 02062212 A2 | 8/2002 |
| WO | 03082091 A2 | 10/2003 |
| WO | 2005046559 A2 | 5/2005 |
| WO | 2006061169 A1 | 6/2006 |
| WO | 2006127841 A2 | 11/2006 |
| WO | 2007000425 A2 | 1/2007 |
| WO | 2007056592 A2 | 5/2007 |
| WO | 2007089537 A1 | 8/2007 |
| WO | 2007149533 A2 | 12/2007 |
| WO | 2008036658 A2 | 3/2008 |
| WO | 2008048556 A2 | 4/2008 |
| WO | 2008048582 A1 | 4/2008 |
| WO | 2008048583 A1 | 4/2008 |
| WO | 2008048584 A1 | 4/2008 |
| WO | 2008048585 A1 | 4/2008 |
| WO | 2008048586 A1 | 4/2008 |
| WO | 2008048587 A1 | 4/2008 |
| WO | 2008064254 A2 | 5/2008 |
| WO | 2008091320 A2 | 7/2008 |
| WO | 2008103175 A1 | 8/2008 |
| WO | 2008112078 A2 | 9/2008 |
| WO | 2008112078 A3 | 10/2008 |
| WO | 2008144693 A1 | 11/2008 |
| WO | 2008144695 A1 | 11/2008 |
| WO | 2008144697 A1 | 11/2008 |
| WO | 2008144698 A1 | 11/2008 |
| WO | 2008153689 A1 | 12/2008 |
| WO | 2008153819 A1 | 12/2008 |
| WO | 2009016636 A2 | 2/2009 |
| WO | 2009032399 A1 | 3/2009 |
| WO | 2009032400 A1 | 3/2009 |
| WO | 2009035759 A1 | 3/2009 |
| WO | 2009088983 A2 | 7/2009 |
| WO | 2009089028 A2 | 7/2009 |
| WO | 2009089029 A2 | 7/2009 |
| WO | 2010111505 A2 | 9/2010 |
| WO | 2011014704 A2 | 2/2011 |
| WO | 2011068648 A2 | 6/2011 |
| WO | 2013016363 A2 | 1/2013 |

(56) References Cited

FOREIGN PATENT DOCUMENTS

| WO | 2013184896 A1 | 12/2013 |
|---|---|---|
| WO | 2018085600 A1 | 5/2018 |

OTHER PUBLICATIONS

Application and File history for U.S. Appl. No. 13/465,570, filed May 7, 2012.
Application and File history for U.S. Appl. No. 14/187,414, filed Feb. 24, 2014.
Application and File history for U.S. Appl. No. 15/830,415, filed Dec. 4, 2017.
Application and File history for U.S. Appl. No. 16/507,380, filed Jul. 10, 2019.
Application and File history for U.S. Appl. No. 11/685,617, filed Mar. 13, 2007.
Application and File history for U.S. Appl. No. 11/266,468, filed Sep. 15, 2016.
Application and File history for U.S. Appl. No. 11/800,453, filed Mar. 13, 2013.
Bott, et al., "Impact of Smoking on the Metabolic Action of Subcutaneous Regular Insulin in Type 2 Diabetic Patients," Horm. Metab. Res., vol. 37, 2005, pp. 445-449.
Chase, et al., "The Use of Insulin Pumps With Meal Bolus Alarms in Children with Type 1 Diabetes to Improve Glycemic Control," Diabetes Carem, vol. 29, No. 5, May 2006, pp. 1012-1015.
"Compare Insulin Pump for Diabetes," Printed from www.diabetesnet.com/diabetes-technology/insulin-pump-models.php, Jun. 18, 2009, 4 pages.
Examination Report for EP Application No. 14775822.1, mailed on Jan. 4, 2019, 4 pages.
Extended European Search Report for Application No. 14775822.1, mailed on Nov. 21, 2016, 9 pages.
International Preliminary Report on Patentability for Application No. PCT/US2008/002536, mailed on Sep. 15, 2009, 9 pages.
International Preliminary Report on Patentability for Application No. PCT/US2008/006801, mailed on Dec. 1, 2009, 9 pages.
International Search Report and Written Opinion for PCT Application No. PCT/US2008/002536 mailed on Sep. 4, 2008, 12 pages.
International Search Report and Written Opinion for PCT Application No. PCT/US2008/006449 mailed on Oct. 10, 2008, 17 pages.
International Search Report and Written Opinion for PCT Application No. PCT/US2008/006801, mailed on Oct. 30, 2008, 17 pages.
International Search Report and Written Opinion for PCT Application No. PCT/US2015/042881 mailed on Nov. 11, 2015, 11 pages.
Lehmann, et al., "Combining rule-based reasoning and mathematical modeling in diabetes care," Artificial Intelligence in Medicine, vol. 6, 1994, pp. 137-160.

Hildebrandt P., "Subcutaneous Absorption of Insulin in Insulin—Dependent Diavetic patients. Influence of Species Physico-Chemical properties of Insulin and Physiological factors," Danish Medical Bulletin, Aug. 1991, 10 pages.
Office Action mailed Apr. 4, 2018 for European Application No. 14775822.1, 4 pages.
Office Action mailed May 25, 2010 for European Application No. 08779626.4, 7 pages.
Office Action mailed Apr. 7, 2010 for European Application No. 08767934.6, 3 pages.
Plougmann, et al., "DiasNet—a diabetes advisory system for communication and education via the internet," International Journal of Medical Informatics, vol. 64, 2001, pp. 319-330.
Puckett, et al., "A model for multiple subcutaneous insulin injections developed from individual diabetic patient data," vol. 269, 1995, p. E1115-E1124.
Smith Medical MD Inc., "Deltec Cozmo, Personalized Insulin Pump, Starting Guide," http://web.archive.org/web/20041207133223/http://www.cozmore.com/Library/-upload/starting.sub.--guide.sub.--032004.pdf, XP002497833, Dec. 7, 2004, pp. 1-83.
Stapel E., "Converting Between Decimals, Fractions, and Percents," Purplemath, 2006, 9 pages, Available at http://www.purplemath.com/modules/percents2.htm, 2006.
Trjanoski, et al., "Pharmacokinetic Model for the Absorption of Subcutaneously Injected Soluable Insulin and Monomeric Insulin Analogues," Biomedizinische Technik, vol. 38, No. 9. Sep. 1, 1993, pp. 224-231.
Wach, et al., "Numerical Approximation of Mathematical Model for Absorption of Subcutaneously Injected Insulin," Med & Biol. Eng & comput., vol. 33, 1995, pp. 18-23.
Walsh, et al., "Diabetes Technology—Concept 1: Super Bolus," available at Diabetes Technology—Concept 1: Super Bolus available at http://www.diabetesnet.com/diabetes.sub.-technology/super.sub.--bbolus.ph-p>, Sep. 17, 2007, 3 pages.
Walsh J., et al., "Select & Test Your Correction Factor," Pumping Insulin, Fourth Edition, Chapter 13, 2006, 10 Pages.
Walsh J., et al., "Select & Test Your Basal Rates," Pumping Insulin, Fourth Edition, Chapter 11, 2006, 30 Pages.
Walsh J., et al., "Select & Test Your Carb Factor," Pumping Insulin, Fourth Edition, Chapter 12, 2006, 32 Pages.
Walsh J., et al., "Pumping Insulin: Everything you need for Success on a Smart insulin Pump," Torrey Pines Press, San Diego, ISBN 1-884804-86-1, 2006, 3 pages.
Wikipedia.com, "Wikipedia's definition for "basal rate"," printed from wikipedia.com on Jun. 12, 2009, 1 page.
Wilinska, et al., "Insulin Kinetics in Type-1 Diabetes: Continuous and Bolus Delivery of Rapid Acting Insulin," IEEE Transaction s on Biomedical Engineering, vol. 52, No. 1, Jan. 2005, pp. 3-12.

\* cited by examiner

INSULIN PUMP BASED EXPERT SYSTEM

RELATED APPLICATIONS

This application is a continuation of U.S. application Ser. No. 16/560,555 filed Sep. 4, 2019, which in turn is a continuation of U.S. application Ser. No. 15/830,415 filed Dec. 4, 2017, now U.S. Pat. No. 11,298,053 issued Apr. 12, 2022, which in turn is a continuation of U.S. application Ser. No. 14/187,414 filed Feb. 24, 2014, now U.S. Pat. No. 9,833,177 issued Dec. 5, 2017, which in turn application is a continuation of U.S. application Ser. No. 13/465,570 filed May 7, 2012, now U.S. Pat. No. 8,657,779 issued Feb. 25, 2014, which in turn is a division of U.S. application Ser. No. 11/755,480 filed May 30, 2007, now U.S. Pat. No. 8,221,345 issued Jul. 17, 2012, each of which is hereby fully incorporated herein by reference.

TECHNICAL FIELD

The field generally relates to patient insulin management devices and, in particular, but not by way of limitation, to systems, devices and methods for managing insulin therapy.

BACKGROUND

People who suffer from diabetes require insulin to keep their blood glucose level as close as possible to normal levels. It is essential for people with diabetes to manage their blood glucose level to within a normal range. Complications from diabetes can include heart disease (cardiovascular disease), blindness (retinopathy), nerve damage (neuropathy), and kidney damage (nephropathy). Insulin is a hormone that reduces the level of blood glucose in the body. Normally, insulin is produced by beta cells in the pancreas. In non-diabetic people, the beta cells release insulin to satisfy two types of insulin needs. The first type is a low-level of background insulin that is released throughout the day. The second type is a quick release of a higher-level of insulin in response to eating. Insulin therapy replaces or supplements insulin produced by the pancreas.

Conventional insulin therapy typically involves one or two injections a day. The low number of injections has the disadvantage of allowing larger variations in a person's insulin levels. Some people with diabetes manage their blood glucose level with multiple daily injections (MDI). MDI may involve more than three injections a day and four or more blood glucose tests a day. MDI offers better control than conventional therapy. However, insulin injections are inconvenient and require a diabetic person to track the insulin doses, the amount of carbohydrates eaten, and their blood glucose levels among other information critical to control.

It is important for a diabetic person to be treated with the proper amount of insulin. As discussed previously, high blood sugar can lead to serious complications. Conversely, a person with low blood sugar can develop hypoglycemia. Ideally, insulin therapy mimics the way the body works. An insulin pump is one way to mimic the body's insulin production. An insulin pump can provide a background or basal infusion of insulin throughout the day and provide a quick release or bolus of insulin when carbohydrates are eaten. If a person develops high blood sugar, a correction bolus can be delivered by the pump to correct it. While insulin pumps improve convenience and flexibility for a diabetic person, they can be sophisticated devices. Some insulin pumps can be difficult to program. Proper use of an insulin pump requires a user to go through a learning curve to properly treat their diabetes using the insulin pump.

SUMMARY

This document discusses, among other things, devices and methods for managing insulin therapy. A device example includes a pump configured to deliver insulin, an input configured to receive blood glucose data, a user interface, and a controller communicatively coupled to the pump, the input, and the user interface. The controller includes a blood glucose data module to compare the blood glucose data to a target blood glucose level for an insulin pump user. The controller is configured to present a question related to the blood glucose level via the user interface when the blood glucose level is different than the target blood glucose level, receive a response to the question via the user interface, and present a recommended user action based at least in part on the response.

A method example includes receiving blood glucose data into a device that includes an insulin pump, presenting a question related to a blood glucose level of an insulin pump user when determining, from the blood glucose data, that the blood glucose level is different from a target blood glucose level, receiving at least one response to the question into the insulin pump device, and presenting a recommended action for a user to take based, at least in part, on the response.

A system example includes a first device and a second device. The first device includes a pump configured to deliver insulin, an input that includes a communication port configured to receive blood glucose data, a user interface, and a controller communicatively coupled to the pump mechanism, the input, and the user interface. The controller includes a blood glucose data module configured to compare the blood glucose data to a target blood glucose level for an insulin pump user. The controller is configured for presenting a question related to the blood glucose level when the blood glucose level is different from a target blood glucose level, receiving a response to the question via the user interface, and presenting a recommended action for the user to take based at least in part on the response. The second device includes a user interface, a processor that includes a rule development module configured for developing the rule via the user interface, and a communication port configured to communicate the rule to the first device.

This summary is intended to provide an overview of the subject matter of the present patent application. It is not intended to provide an exclusive or exhaustive explanation of the invention. The detailed description is included to provide further information about the subject matter of the present patent application.

DETAILED DESCRIPTION

The following detailed description includes references to the accompanying drawings, which form a part of the detailed description. The drawings show, by way of illustration, specific embodiments in which the invention may be practiced. These embodiments, which are also referred to herein as "examples," are described in enough detail to enable those skilled in the art to practice the invention. The embodiments may be combined, other embodiments may be utilized, or structural, logical and electrical changes may be made without departing from the scope of the present invention. The following detailed description is, therefore, not to be taken in a limiting sense, and the scope of the present invention is defined by the appended claims and their equivalents.

In this document, the terms "a" or "an" are used, as is common in patent documents, to include one or more than one. In this document, the term "or" is used to refer to a nonexclusive or, such that "A or B" includes "A but not B," "B but not A," and "A and B," unless otherwise indicated. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

Figure 1A:
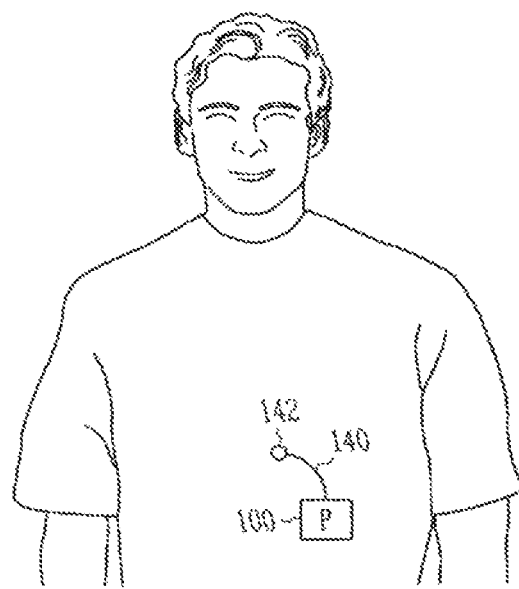
FIGS. 1A and 1B illustrate portions of a device that includes an insulin pump.
Figure 1B:
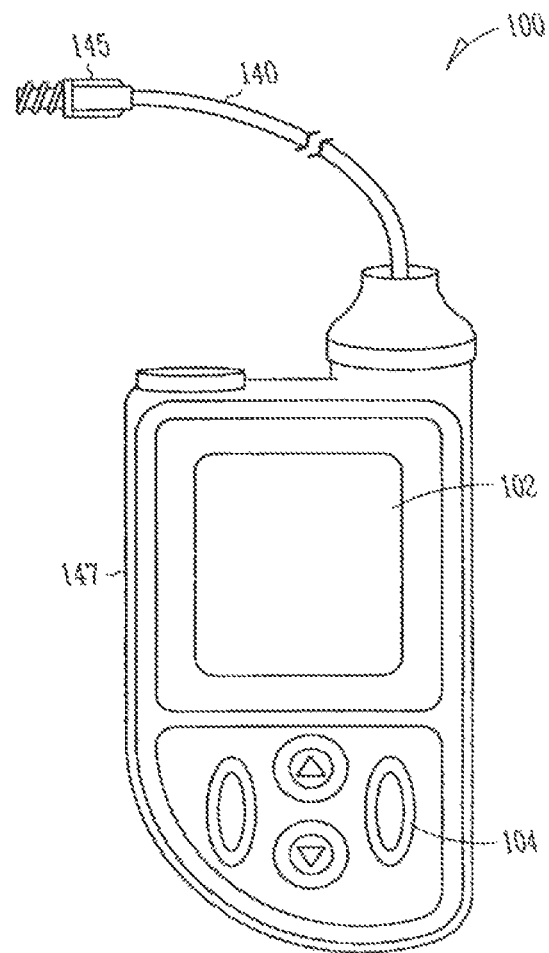

FIGS. 1A and 1B illustrate portions of a device 100 that includes an insulin pump. The device 100 includes a cassette or cartridge of insulin. The cartridge is connectable to infusion tubing 140 connectable to a patient such as by a Luer lock 145 or infusion set 142. The device 100 includes a display 102 and a user interface that may include the display 102 and include one or more keys 104. Because proper use of an insulin pump requires a user to go through a learning curve to properly treat their diabetes using the pump, it is desirable for a pump to provide assistance to the user, whether the user is a diabetic patient, a caregiver, or a clinician. Providing an expert system in an insulin pump device will provide assistance to the user to effectively treat their diabetes using the insulin pump device.

Figure 2:
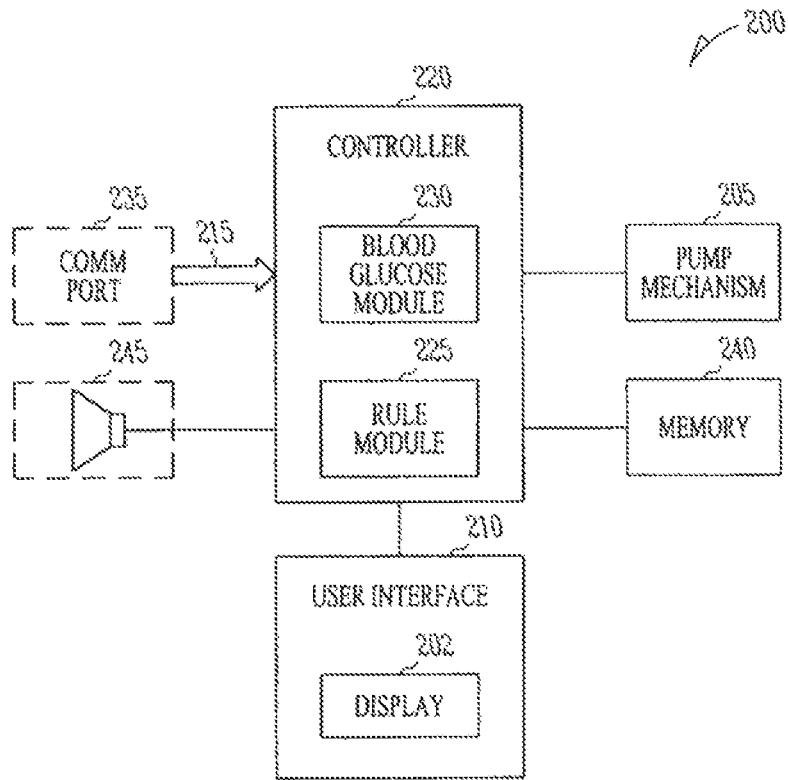
FIG. 2 is a block diagram of an example of portions of an insulin pump device.

FIG. 2 is a block diagram of an example of portions of an insulin pump device 200. The insulin pump device 200 includes a pump 205 or pump mechanism to deliver insulin to a subject, such as a positive displacement pump for example. The insulin pump device 200 also includes a user interface 210, an input 215, and a controller 220. The user interface 210 receives manual input from a user and may include one or more pushbuttons or a keypad. The user interface 210 may include a display 202 to provide instructions to the user. The user of the device may be a clinician or a diabetic patient. The display 202 may include a touchscreen.

The input 215 is configured to receive blood glucose data of a patient or subject. The input 215 may be coupled to a blood glucose monitor (GM) included in the insulin pump device 200 or the input 215 may include a communication port to receive the blood glucose data from a second separate device. In some embodiments, the communication port 235 is a wireless communication port configured to receive the blood glucose data from the separate device wirelessly. If the GM is a continuous GM, the continuous GM automatically collects the sampled blood glucose data in real time. The insulin pump device 200 may receive the blood glucose in real time as it is obtained or communicated at a later time. If the data is communicated at a later time, a timestamp may be included with the blood glucose data to indicate at what time the data was collected. In some embodiments, the input 215 is coupled to the user interface 210, and the user may manually input the data into the insulin pump device 200 through a keypad included in the user interface 210.

In some examples, the GM may require a prompt from the user to begin a blood glucose data measurement to obtain the blood glucose data. For example, the GM may require diabetes test strips to take a blood glucose measurement. The controller 220 recurrently presents a prompt to the user to begin a blood glucose measurement using the GM and obtain blood glucose data. In certain examples, the prompt is presented periodically. The prompt may be presented via the display 202. The prompt may be presented by activating a light emitting diode (LED) included in the insulin pump device 200. In some examples, the prompt is presented by audibly such as by a transducer or by a speaker instructing the user. The user then provides a new test strip to the GM when prompted during the correction factor test. In another example, the GM may include a drum of diabetes test strips and the user advances the drum to a fresh or unused test strip when prompted by the controller 220.

If the insulin pump device 200 includes a continuous GM, the input 215 may be coupled to blood glucose sensor circuit. The blood glucose sensor circuit includes a blood glucose sensor to produce a blood glucose signal representative of a blood glucose level of the patient. The blood glucose sensor may sense blood glucose concentration from blood or interstitial fluid. The blood glucose sensor circuit may include a sensor interface circuit to sample the blood glucose signal and may provide additional signal processing such as filtering or amplification for example. The blood glucose sensor circuit may provide sampled blood glucose data to the input 215. A description of a blood glucose sensor circuit can be found in Steil et al., U.S. Pat. No. 6,558,351, filed Jun. 1, 2000.

The controller 220 is operatively coupled to the pump mechanism 205, the input 215, and the user interface 210. The controller 220 can be implemented using hardware circuits, firmware, software or any combination of hardware, firmware and software. Examples, include a microcontroller, a logical state machine, and a processor such as a microprocessor, application specific integrated circuit (ASIC), or other type of processor. The controller 220 is configured to perform or execute a function or functions. Such functions correspond to modules, which are software, hardware, firmware or any combination thereof. Multiple functions are performed in one or more modules.

The controller 220 monitors the blood glucose data of the subject. The controller 220 includes a blood glucose data module 230. The blood glucose data module 230 uses the blood glucose data to determine whether a blood glucose level of the subject is different from a target blood glucose level. The target blood glucose level may include a specified range of blood glucose levels and the blood glucose data module 230 may determine whether the blood glucose data indicates the blood glucose of the pump user is outside of a specified range of blood glucose levels. Being outside of a range may include having a blood glucose level that is too high or too low. The blood glucose data module 230 may determine whether a blood glucose level is above an acceptable range of higher blood glucose level, or below an acceptable range of low blood glucose levels. The target or range may be stored in memory and be a programmable parameter available to the blood glucose data module 230.

A clinician would specify the range of blood glucose levels for the patient. The range would depend on various factors for the patient such as weight, age, and level of activity of the patient for example.

If the blood glucose data module 230 determines that the blood glucose level of the subject is different from the target or the specified range of blood glucose levels, the controller 220 presents one or more questions related to the blood glucose level via the user interface 210. Preferably, the question is presented using the display 202. However, in some examples, the question may be presented audibly. Presenting the question audibly may be useful if the insulin pump user has difficulty seeing the display 202. The questions are designed to help a user to properly treat their diabetes using the insulin pump device 200 and even by programming the insulin pump device 200. In some examples, the controller 220 presents different questions according to different blood glucose levels. For example, the controller 220 may present different questions according to whether the blood glucose level of the patient is above 200 mg/dl, or above 300 mg/dl, or above 400 mg/dl. The clinician may program the different levels into the insulin pump device 200.

The user responds to the question through the user interface 210. Based at least in part on one or more responses, the controller 220 displays at least one recommended action for the user to take. As is discussed below, the recommended action may involve various user actions such as troubleshooting the insulin pump device 200, delivering insulin using the insulin pump device 200, initiating a measurement or test using the insulin pump device 200, or making lifestyle changes for example. In some examples, the recommended action for display may include contacting a physician. In some examples, the recommended action may be different according to the blood glucose level of the patient. For example, the controller 220 may present different actions according to whether the blood glucose level of the patient is above 200 mg/dl, or above 300 mg/dl, or above 400 mg/dl.

If the question is presented using a display 202, the device may include an alarm circuit 245 coupled to the controller 220 to draw the attention of the user to the display 202. The alarm circuit 245 may include an audible alarm, a visual indication such as a flashing light or flashing icon on the display, or the alarm circuit may mechanically vibrate the insulin pump device to draw attention of the user. The controller 220 activates the alarm circuit 245 if it is determined that the blood glucose level of the subject is outside of the specified range of blood glucose levels.

Figure 3:
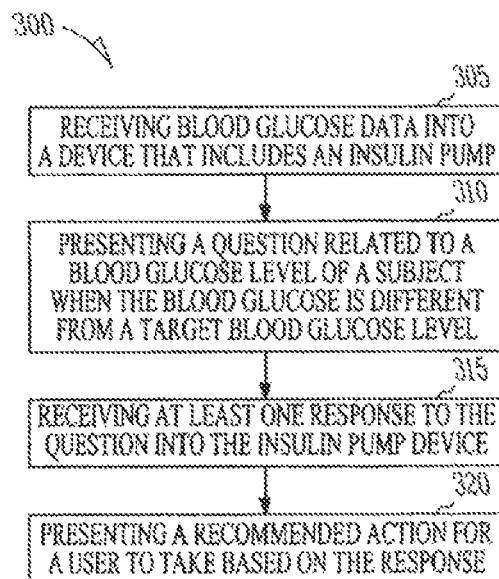
FIG. 3 shows an example of a method for managing insulin therapy.

FIG. 3 shows an example of a method 300 for managing insulin therapy. At block 305, blood glucose data is received into an insulin pump device 200. At block 310, at least one question related to a blood glucose level of a patient is presented when determining, from the blood glucose data, that the blood glucose level is outside of a range of blood glucose levels. The question may be presented on a display 202 included with the insulin pump device 200, or the question may be transmitted to a second device for display, such as a computer for example. This may be useful if a display 202 on the insulin pump device 200 is difficult for the user to read. In some examples, the second device presents the question audibly. The insulin pump and the second device may communicate wirelessly such as by radio frequency (RF) or infrared red (IR) communication. At block 315, at least one response to the question is received into the insulin pump device 200. The response may be received through a user interface. At block 320, at least one recommended action is presented for a user to take based, at least in part, on the response. The action may be presented audibly or visually, such as by a display for example.

Figure 4:
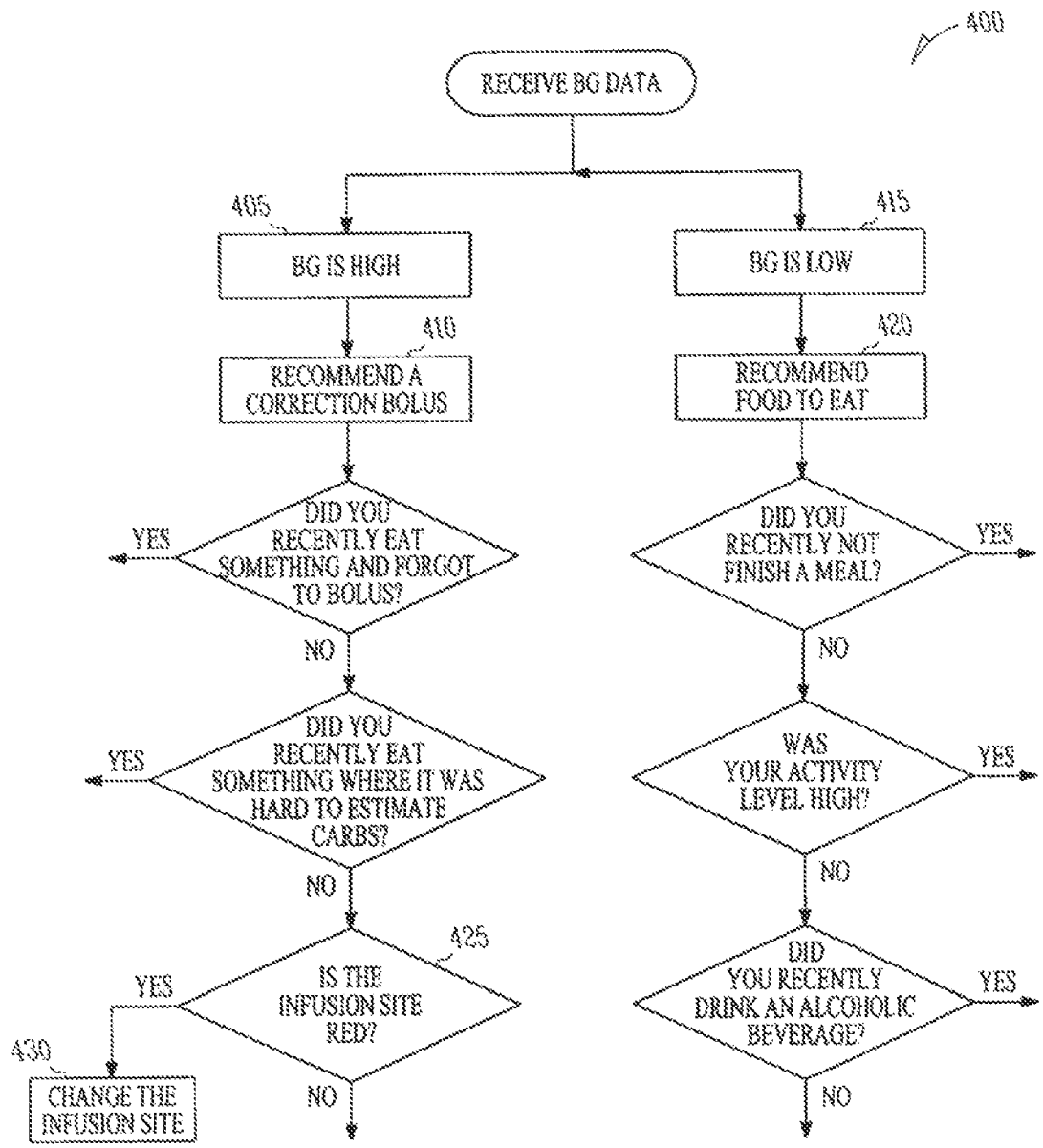
FIG. 4 shows a portion of an example of a decision tree to determine one or more questions for the user of an insulin pump device.

Returning to FIG. 2, in some embodiments, the controller 220 includes a rule module 225 to apply at least one rule to the blood glucose data to determine the question to be presented. In some embodiments, the rule includes a decision tree. FIG. 4 shows a portion of an example of a decision tree 400 to determine one or more questions for the user of the insulin pump device 200. In certain examples, the decision tree 400 may implemented with a series of IF-Then logic statements. The controller 220 traverses the decision tree 400 using various information such as the blood glucose data, responses from the user, or other data. If the blood glucose is high, the left portion of the decision tree 400 is traversed at block 405. The controller 220 may display a recommended action, such as the user taking a correction bolus at block 410, before asking one or more questions. If the blood glucose is low, the right portion of the decision tree 400 is traversed at block 415. The controller 220 may display a recommended action, such as the user eating food at block 420 before asking one or more questions. The controller 220 may display a picture or icon of food when making the recommendation.

In some examples, the rule module 225 applies the rule to the blood glucose data and to at least one user response to the question to determine the recommended action for display. For example, using the decision tree 400, if the blood glucose level is high, the controller 220 may display a question asking if the infusion site is red at block 425. If the user interface 210 receives a response from the user that the site is red, the controller 220 may display a recommendation that the user change the infusion site at block 430.

In some embodiments, the rule module 225 may include a look-up table stored in a memory. For example, if the blood glucose is low, the look up table may include a question as to whether the patient had a high activity level. If the user interface 210 receives a response that the activity level was high, the look up table includes a recommended action corresponding to a table entry for low blood glucose and high activity. The table entry may include a recommended action that the patient eat before the activity or lower a programmable basal rate of insulin before or during the activity. The table may include multiple dimensions to take into account multiple factors, responses, or other data. In some examples, the rule module 225 assigns weights to corresponding table entries. For example, receiving a response that the infusion set has visible blood may by weighted as a stronger indication to change the infusion site than if a response is received that the infusion site is red. In some examples, the rule module 225 uses one or more fuzzy logic rules to determine the question for display and any recommended action. The fuzzy logic rules may be used to blend any weighted questions, responses, or actions. In some examples, the rule module 225 uses a rule involving application of artificial intelligence methods to determine the questions and the actions to be presented.

In some examples, the rule module 225 may apply the rule to the blood glucose data and present a recommendation that the user initiate at least one blood glucose measurement. The measurement may be made using a second separate device that includes a GM, or the action may recommend making the measurement with the insulin pump device 200 if the device includes a GM.

Note that application of the rule by the rule module 225 may result in a series of questions displayed, responses by the user, and recommend actions. For example, the insulin pump device 200 may receive an indication that a recommended action was taken. The rule module 225 may apply the rule to the blood glucose data, the response to the question, and the indication that the action was taken to determine at least one of a further question and a further recommended action to be presented.

In some examples, the rule module 225 may apply the rule to the blood glucose data and present a recommendation that the user initiate a basal rate test. Basal rate refers to a type of twenty-four hour background infusion of insulin by an insulin pump that mimics the continuous background release of insulin from a normal pancreas. It is the rate of insulin delivery the patient normally needs independent of the consumption of meals. If the basal rate is inappropriate, blood glucose concentration levels may result that are out of a recommended or desired range. An insulin pump user may go through several iterations of trial and error before finding appropriate basal rates. Because a patient's basal insulin needs may change over time, such as with weight change or with a change in fitness level, basal rate testing may be performed periodically to ensure that an appropriate basal rate is being delivered by an insulin pump. Based on the blood glucose level, the rule module 225 determines that a recommendation to run a basal rate test (by either the insulin pump device 200 or a separate device) should be presented (such as by display). As a result of the basal rate test, the controller may display a recommendation to change a programmable basal rate pattern or profile of the insulin pump device 200. Descriptions of devices and methods that perform a basal rate test are found in Blomquist et al., "Basal Rate Testing Using Frequent Blood Glucose Input," U.S. patent application Ser. No. 11/685,617, filed Mar. 13, 2007, which is incorporated herein by reference.

In some examples, the rule module 225 may apply the rule to the blood glucose data and present a recommendation that the user initiate a carbohydrate ratio test if the blood glucose level is outside a desired range. A carbohydrate ratio refers to the amount of carbohydrates covered by a unit of insulin. It is sometimes referred to as a carbohydrate factor, or carb factor, and is typically specified as grams of carbohydrates per unit of insulin. The insulin pump device 200 may use the carbohydrate ratio to automatically determine a carbohydrate insulin bolus amount required to match a number of carbohydrates ingested by the patient, or at least to keep post-meal blood glucose within a range that is healthy for a patient. For example, the patient may plan to eat seventy grams of carbohydrates. If the carbohydrate ratio is ten grams of carbohydrates per unit of insulin, the insulin pump device 200 would determine that seven units of insulin are required to cover the carbohydrates.

The appropriate carbohydrate ratio may vary from person to person, yet it is important for an insulin pump to use an appropriate carbohydrate ratio. If a carbohydrate ratio is too small, the pump may determine a carbohydrate bolus that is too large for the carbohydrates consumed. This may cause a low blood glucose level within a few hours of the carbohydrate bolus (e.g., the blood glucose level drops below 70 mg/dl). If a carbohydrate bolus is too large, the insulin pump device 200 may determine a carbohydrate bolus that is too small for the carbohydrates consumed. This may cause a high blood glucose level within a few hours of a carbohydrate bolus. Based on the blood glucose level, the rule module 225 determines that a recommendation to run a carbohydrate ratio test should be presented. As a result of the carbohydrate ratio test, the controller 220 may present a recommendation to change a carbohydrate insulin bolus pattern or profile delivered by the insulin pump device 200.

For example, the controller 220 may recommend a carbohydrate bolus pattern that includes an extended carbohydrate bolus or a combination bolus. Descriptions of devices and methods that perform a carbohydrate ratio test are found in Blomquist, "Carbohydrate Ratio Testing Using Frequent Blood Glucose Input," U.S. patent application Ser. No. 11/679,712, filed Feb. 27, 2007, which is incorporated herein by reference.

In some examples, the rule module 225 may apply the rule to the blood glucose data and present a recommendation that the user initiate a correction factor test. A correction factor refers to the amount in drop in blood sugar, or blood glucose, for one unit of insulin. It is measured in milligrams per deciliter (mg/dl) per unit in the U.S. and in millimoles (mmol) per unit in other countries. The insulin pump device 200 may use the correction factor to automatically determine a bolus amount required for a high reading or a reduction in a meal bolus for a below-target reading. The insulin pump device 200 may also use the correction factor to calculate the amount of carbohydrates a patient should eat to bring low blood sugar up to a target blood sugar level. An appropriate correction factor brings a high blood glucose reading down using an automatically determined correction bolus without a risk of going low.

The appropriate correction factor varies from person to person. It is important for an insulin pump to use an effective correction factor. If a correction factor for a pump is set too high, the blood glucose may not actually be dropping as much as estimated and could lead to high blood glucose levels. If the correction factor is set too low, a correction bolus may provide too much insulin and result in a low blood glucose level. As a result of the carbohydrate ratio test, the controller 220 may display a recommendation to change an insulin correction bolus pattern or profile, such as to include an extended bolus or a combination bolus for example. Descriptions of devices and methods that perform a carbohydrate ratio test are found in Blomquist et al., "Correction Factor Testing Using Frequent Blood Glucose Input," U.S. patent application Ser. No. 11/626,653, filed Jan. 24, 2007, which is incorporated herein by reference.

In some embodiments, the rule module 225 may receive an updated or new rule or a modification to the rule. In certain embodiments, the insulin pump device 200 includes a communication port 235 coupled to the input 215. The communication port 235 receives the rule into the insulin pump device 200 from a second separate device. In some examples, the communication port 235 is a wireless port and receives the rule wirelessly. The second device may be a computer or a personal data assistant (PDA). The second device may provide an environment (e.g., such as through software) for a diabetes professional, clinician, or other caregiver to customize the rule. In some examples, the environment allows the clinician to customize a decision tree or look up table.

Figure 5:
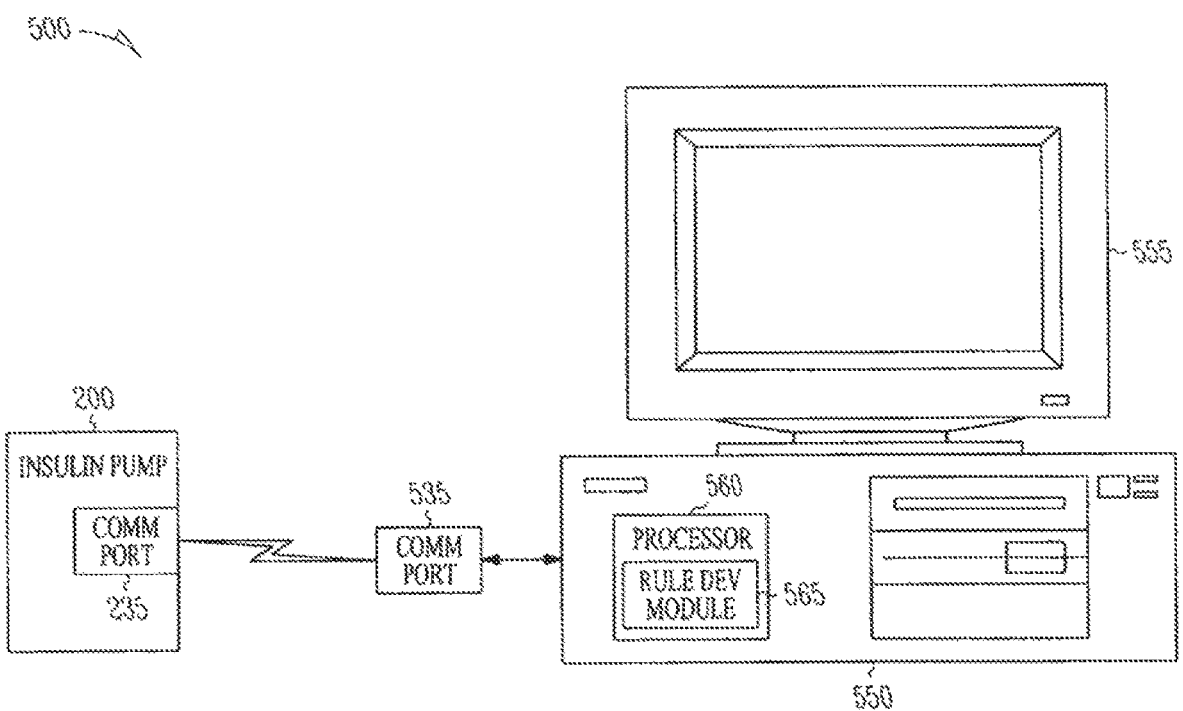
FIG. 5 shows an example of a portion of a system that provides an environment to customize a rule for an insulin pump device.

FIG. 5 shows an embodiment of a portion of a system 500 that provides an environment to customize rules in the rule module 225. The system 500 includes an insulin pump device 200 and a computing device 550. The insulin pump device 200 includes a communication port 235 to communicate information with the computing device 550. The communication port 235 shown is a wireless port that communicates wirelessly with the computing device 550, such as a radio frequency (RF) port or infrared (IR) port for example. The communication port 235 may receive blood glucose data from a third device, such as a GM for example. In certain examples, the insulin pump device 200 receives the blood glucose data from a GM when the GM is communicatively coupled to the communication port 235. The insulin pump device 200 is able to communicate information with the computing device 550 when the GM is not communicatively coupled to the insulin pump device 200. In some examples, the communication port 235 may be a wired port, such as a serial port for example, to communicate with the computing device 550.

The computing device 550 may be a personal computer (PC), laptop computer, or a personal data assistant (PDA). The computing device 550 includes a user interface 555 that includes a display and may include at least one of a keyboard or keypad and a computer mouse. The computing device 550 also includes a processor 560 communicatively coupled to the user interface 555. The processor 560 can be a microprocessor, application specific integrated circuit (ASIC), or other type of processor.

The processor 560 includes a rule development module 565 that provides doctors or clinical experts the ability to develop and generate a new rule or rule set or modify rules via the user interface 555. The computing device 550 includes software that provides a flexible framework to create or modify rules such as by updating a graphical decision tree, a multidimensional table, or other type of logical rule. The software may be included in a computer readable medium, such as a compact disc (CD) for example, or the software may be downloaded to the computing device 550 from remote storage, such as from a server for example. The rule development module 565 develops a rule to be applied to the blood glucose data received into the insulin pump device 200, and may develop a rule that is also applied to at least one of physiologic data, demographic data, patient lifestyle data, insulin delivery history data, and blood glucose history data to generate a recommended action. The computing device 550 includes a communication port 535 to communicate information with the insulin pump device 200. The computing device 550 uses the communication port 535 to communicate the rule to the insulin pump device 200.

Once a rule is developed, the doctor or clinical expert could publish or otherwise share a rule or set of rules. In some embodiments, rule sets can be stored in remote storage, such as a server for example. The computing device 550 may be connected to a communication network, such as the internet or a cell phone network for example. A doctor or clinical expert may download a rule or rule set from the remote storage and either download the rule set directly from the computing device 550 into the insulin pump device 200 or modify the rule or rule set before downloading the modified rule or rule set to the insulin pump device 200.

Returning to FIG. 2, in some embodiments, the user interface 210 and the input 215 receive modifications to the rule that are entered into the insulin pump device 200 manually by the user via the user interface 210. For example, the user may step through the rule with the aid of the display 202. The user may then alter the rule with a keypad included in the user interface 210. For example, the user may enter a new look up table entry using the key pad, or add another branch to a decision tree or edit a branch of the decision tree. In certain embodiments, an entire new rule or rule set is entered manually into the insulin pump device 200 via the user interface 210.

In some embodiments, the insulin pump device 200 stores data to track effectiveness of a new rule or modified rule. For example, the insulin pump device 200 may track the number of times the blood glucose level of the patient returned to the target blood glucose level or to within the target range of levels after application of the rule. The effectiveness may be displayed as a percentage or as X successes out of Y applications on either a display 202 of the insulin pump or uploaded and displayed on a separate device, such as the computing device 550 in FIG. 5 for example.

If a rule or rule set is downloaded into multiple devices, the effectiveness of the rule set for multiple device may be tracked. The stored data related to the effectiveness may be uploaded to a remote server and the server tracks the overall effectiveness of the rule over the multiple devices. The overall effectiveness may be useful to a clinician in determining whether to download a particular rule or rule set to the insulin pump device 200.

In some embodiments, controller 220 determines a rate of change of a blood glucose level of the subject from the blood glucose data. For example, the controller 220 may determine that the blood glucose concentration level is increasing or decreasing at a rate of 2 to 4 mg/dl/min (milligrams per deciliter per minute). The rule module 225 may apply one or more rules to the rate of change of a blood glucose level to determine at least one of a question for display or one or more recommended actions for display. For example, the blood glucose level of the user may not be high, but the rate of change of blood glucose may be increasing at such a rate to indicate there is a risk of the blood glucose level going high. Conversely, the blood glucose level of the user may not be below a blood glucose target, but the rate of change of blood glucose may be decreasing at such a rate to indicate there is a risk of the blood glucose level going low.

In some examples, the rule module 225 may apply the rules to at least one of the blood glucose data, the rate of change of blood glucose data, and a response to a question to determine a subsequent question or recommended action for display by the controller 220. For example, if the blood glucose level is high and increasing at a certain rate, the rule module 225 may apply the rule to determine that a recommended action to take a correction bolus should be presented before presenting a question. In another example, if the blood glucose level is high and decreasing at a certain rate, the rule module 225 may apply the rule to determine that a recommended action to take a correction bolus should not be displayed and proceed to displaying a question such as whether the patient ate something where it was difficult to estimate the carbohydrates.

According to some embodiments, the controller 220 may display a recommendation that the patient consume carbohydrates if the blood glucose level is low or there is a risk of blood glucose level going low. In some examples, the memory 240 may store a database of food options in association with a known amount of carbohydrates. The recommended action presented by the controller 220 may include displaying a food option for consumption that is included in the database.

In some embodiments, the controller 220 determines an amount of carbohydrates for the patient to consume and presents a food option accordingly. For example, assume that the blood glucose level of a patient is 40 mg/dl below a desired range of blood glucose levels. The correction factor is stored in the insulin pump device 200 and is 1 unit per 80 mg/dl. The controller 220 determines that −0.5 unit of insulin (−40/80) is required to bring the blood glucose level back to the target level or range. Further assume that the carbohydrate ratio of the patient is 20 grams of carbohydrates per unit of insulin (20 g/u). The controller 220 multiplies the amount of insulin by the carbohydrate ratio to determine that the patient should eat 10 grams of carbohydrates [(0.5)(20)]. The insulin calculation module 125 may take into account additional factors such as the health status of the patient and the activity level of the patient in recommending the carbohydrate amount. In some example, the food option may be displayed using an icon or picture of food.

According to some embodiments, the input 215 receives physiologic data into the insulin pump device 200 from a separate second device. The data may be received through the input 215 or another input. In some embodiments, the insulin pump device 200 receives the physiologic data through a communication port 235. In some examples, the insulin pump device 200 receives the physiologic data through the same communication port 235 that receives the blood glucose data. In some examples, the second device includes a temperature monitor and the physiologic data includes a patient temperature. In some examples, the second device includes an activity monitor and the physiologic data includes an indication of a level of patient activity.

The rule module 225 may apply one or more rules to the physiologic data to determine a question for display. The rule module 225 may apply one or more rules to the physiologic data and a response to the question to determine one or more recommended actions for display. In some examples, the rule module 225 may apply one or more rules to the physiologic data, the blood glucose data, at least one question response to determine a question or recommended action for display. The controller 220 displays the questions and recommended actions.

In some embodiments, the insulin pump device 200 includes a memory 240 communicatively coupled to the controller 220. The memory 240 may store demographic data of the subject. The demographic data includes such information as a patient's weight, age, and gender for example. The demographic data may be received from a second device or through the user interface 210. The rule module 225 may apply one or more rules to the demographic data to determine a question to be presented. The rule module 225 may apply one or more rules to the demographic data and a response to the question to determine and/or adjust one or more recommended actions. In some examples, the rule module 225 may apply one or more rules to the demographic data, the blood glucose data, at least one question response to determine a question or recommended action for display.

In some embodiments, the controller 220 adjusts the questions and recommended actions based on the demographic data. For example, the controller 220 may use a different set of questions and recommended actions when the demographic data indicates that the patient is a child than when the demographic data indicates the patient is an adult.

In some embodiments, the memory 240 may store lifestyle data of the subject. The lifestyle data includes such information as whether a patient tends to eat high glycemic index foods, drinks alcohol, smokes, eats a bedtime snack, a health status of the patient, whether the patient is typically under stress, whether the patient tends to be active, and the amount time the patient spends exercising, for example. The lifestyle data may be received from a second device or entered through the user interface 210. The rule module 225 may apply one or more rules to the lifestyle data to determine a question for display. The rule module 225 may apply one or more rules to the lifestyle data and a response to the question to determine one or more recommended actions for display. In some examples, the rule module 225 may apply one or more rules to the lifestyle data, the blood glucose data, at least one question response to determine a question or recommended action for display.

A recommended action may include a change to at least one aspect of the patient's lifestyle, such as to skip the bedtime snack or to eat lower glycemic index meals, for example. In some examples, the recommended action may include recommending patient training. In certain examples, the insulin pump device 200 may present a recommendation that the patient be trained in carbohydrate counting. In certain examples, the insulin pump device 200 may recommend that the patient be trained in managing their exercise. In certain examples, the insulin pump device 200 may recommend that the patient be trained in using the insulin pump when the patient is sick. In certain examples, the insulin pump device 200 may recommend that the patient be trained in proper infusion site care.

In some embodiments, the memory 240 may store insulin delivery history data of the patient. Insulin delivery history data may include a time duration since the last meal bolus, how long since the cartridge was changed, and whether there have been any recent changes to programming parameters and what those changes were for example. The rule module 225 may apply one or more rules to the insulin delivery history data to determine a question to be presented. The rule module 225 may apply one or more rules to at least one of the insulin delivery history data, the blood glucose data, and a response to a question to determine one or more recommended actions.

In some embodiments, the memory 240 may store blood glucose history data of the subject. Blood glucose history data may include blood glucose data from a previous time period, such as two hours or 24 hours in the past for example. The data may be received from a GM included in the insulin pump device 200 or from a GM included in a separate device. In some examples, the blood glucose history data may be received from a separate computing device such as a PC, laptop, or PDA configured to communicate with the insulin pump device 200. The controller 220 may generate a prompt to download blood glucose history data from the second separate device, such as a prompt on a display 202, an LED prompt, or an audible prompt. The rule module 225 may apply one or more rules to the blood glucose history data to determine a question to be presented. The rule module 225 may apply one or more rules to at least one of the blood glucose history data, the blood glucose data collected in real time, and a response to a question to determine one or more recommended actions.

The patient may experience trouble with the insulin pump device 200 itself. According to some embodiments, the recommended action presented by the controller 220 includes actions for troubleshooting the insulin pump device 200. If the blood glucose level is low, the recommended actions may include checking or changing the insulin cartridge, the infusion set, the infusion set tubing, and/or the infusion site. For example, if the insulin pump device 200 stores the time since the cartridge was changed, the rule module 225 may determine that it is time for a new cartridge and display instructions to check whether the cartridge is low or change the cartridge. If it has been a short time since the cartridge was changed, the rule module 225 may eliminate the cartridge as the problem and display instructions to check or change the infusion set or the infusion site.

In another example, the user may respond that the cartridge was checked. The rule module 225 may apply the rule to the blood glucose level and the response and eliminate the cartridge as the problem. The insulin pump device 200 and the user may then step through response and actions that instruct the user to troubleshoot the infusion set and site. The controller 220 may also present a recommendation to change the type of insulin. For example, the rule module 225 may determine that the delay for uptake is too slow and recommend that the patient use a type of insulin with faster uptake. The controller 220 may also present a recommendation to change an insulin pump executable program and to see a diabetes professional. The controller may present a question whether the infusion set has visible blood and recommend that the infusion site be changed if there is visible blood. In some examples, the controller 220 may display a device error code and a recommendation to see the diabetes professional rather than present instructions to the user or patient that the pump program should be changed. The diabetes professional interprets the error code to determine the recommended action.

According to some examples, the blood glucose data module 230 may determine from the blood glucose data that a blood glucose level of the subject is at a target blood glucose level or within a specified range of blood glucose levels. The rule module 225 may determine one or more recommend actions for the patient to take that are related to maintaining normoglycemia. The rule module 225 may apply the rule to the blood glucose data and at least one of the physiologic data, the demographic data, the lifestyle data, the blood glucose history data, the insulin delivery history data, question responses, and previous actions taken to make the recommendation. The controller 220 displays the recommended action. For example, the controller 220 may ask lifestyle questions when blood glucose data is in the normoglycemic range. The controller 220 may aggregate insulin pump data and answers to the questions from various times when the blood glucose data values were in range and help the patient identify lifestyle or therapy patterns that promote good glycemic control.

It is to be understood that the above description is intended to be illustrative, and not restrictive. For example, the above-described embodiments (and/or aspects thereof) may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The Abstract of the Disclosure is provided to comply with 37 C.F.R. § 1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own.

The invention claimed is:

1. A method of diabetes therapy, comprising:

delivering insulin to a user with an insulin pump;

receiving sensor glucose data representative of a blood glucose level of a user from a continuous glucose monitor via a wireless connection;

monitoring the sensor glucose data from the continuous glucose monitor while the insulin pump is delivering a basal rate of insulin to the user;

comparing the sensor glucose data to a target low glucose level;

determining a rate of change of the blood glucose level of the user from the sensor glucose data;

generally continuously monitoring the rate of change;

determining based on the generally continuous monitoring of the rate of change that, although the sensor glucose data does not indicate that the glucose level of the user is below the target low glucose level that the rate of change indicates that the glucose level of the user is at risk of going below the target low glucose level due to the basal rate of insulin being delivered to the user;

providing a notification indicating the risk of going below the target low glucose level; and reducing a basal rate of insulin being delivered to the user in response to the risk of going below the target low glucose level.

2. The method of claim 1, wherein providing a notification relating to the risk of going below the target low glucose level includes providing a message relating to a corrective action responsive to the risk of going below the target low glucose level.

3. The method of claim 2, wherein the corrective action is a recommendation to ingest carbohydrates.

4. The method of claim 1, further implementing a corrective action in response to the risk of going below the target low glucose level.

5. The method of claim 4, wherein the implemented corrective action is a recommendation to ingest carbohydrates.

6. The method of claim 1, wherein determining that, although the sensor glucose data does not indicate that the glucose level of the user is below the target low glucose level that the rate of change indicates that the glucose level of the user is at risk of going below the target low glucose level includes applying one or more rules to the rate of change.

7. The method of claim 1, wherein reducing the basal rate of insulin being delivered to the user is in response to a manual instruction from the user to reduce the basal rate of insulin.

8. The method of claim 7, further comprising to presenting a recommendation to reduce the basal rate of insulin to the user and the basal rate of insulin is reduced if the user accepts the recommendation.

9. A method of diabetes therapy, comprising:

delivering insulin to a user with an insulin pump;

receiving sensor glucose data representative of a blood glucose level of a user from a continuous glucose monitor via a wireless connection;

monitoring the sensor glucose data from the continuous glucose monitor while the pump is delivering a basal rate of insulin to the user;

comparing the sensor glucose data to a target low glucose level;
determining a rate of change of the blood glucose level of the user from the sensor glucose data;
generally continuously monitoring the rate of change;
determining, based on the generally continuous monitoring of the rate of change that, although the sensor glucose data does not indicate that the glucose level of the user is below the target low glucose level that the rate of change indicates that the glucose level of the user is at risk of going below the target low glucose level due to the basal rate of insulin being delivered to the user; and
implementing a corrective action in response to the risk of going below the target low glucose level, including reducing a basal rate of insulin being delivered to the user.

10. The method of claim 9, wherein the implemented corrective action is a recommendation to ingest carbohydrates.

11. The method of claim 9, further providing a notification on a user interface relating to the risk of going below the target low glucose level.

12. The method of claim 11, wherein providing a notification relating to the risk of going below the target low glucose level includes providing a message relating to the corrective action.

13. The method of claim 12, wherein the corrective action is a recommendation to ingest carbohydrates.

14. The method of claim 9, wherein determining that, although the sensor glucose data does not indicate that the glucose level of the user is below the target low glucose level that the rate of change indicates that the glucose level of the user is at risk of going below the target low glucose level includes applying one or more rules to the rate of change.

15. The method of claim 9, wherein the basal rate of insulin being delivered to the user is reduced in response to a manual instruction from the user to reduce the basal rate of insulin.

16. The method of claim 15, further comprising presenting a recommendation to reduce the basal rate of insulin to the user and the basal rate of insulin is reduced if the user accepts the recommendation.

* * * * *